United States Patent
Fukuda

(10) Patent No.: US 12,303,312 B2
(45) Date of Patent: May 20, 2025

(54) CONTROL APPARATUS, CONTROL METHOD, AND CONTROL PROGRAM

(71) Applicant: FUJIFILM Corporation, Tokyo (JP)

(72) Inventor: Wataru Fukuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 320 days.

(21) Appl. No.: 18/177,015

(22) Filed: Mar. 1, 2023

(65) Prior Publication Data

US 2023/0218254 A1 Jul. 13, 2023

Related U.S. Application Data

(63) Continuation of application No. PCT/JP2021/030468, filed on Aug. 19, 2021.

(30) Foreign Application Priority Data

Sep. 28, 2020 (JP) .................. 2020-162695

(51) Int. Cl.
*A61B 6/00* (2024.01)
*A61B 6/50* (2024.01)
(Continued)

(52) U.S. Cl.
CPC .............. *A61B 6/502* (2013.01); *A61B 6/481* (2013.01); *A61B 6/482* (2013.01); *A61B 6/5264* (2013.01);
(Continued)

(58) Field of Classification Search
None
See application file for complete search history.

(56) References Cited

U.S. PATENT DOCUMENTS

| 4,482,918 A | 11/1984 | Keyes et al. |
| 2012/0134464 A1 | 5/2012 | Hoernig et al. |

(Continued)

FOREIGN PATENT DOCUMENTS

| JP | 102-063439 A | 3/1990 |
| JP | 2017-104531 A | 6/2017 |
| JP | 2017-143943 A | 8/2017 |

OTHER PUBLICATIONS

International Search Report issued in PCT/JP2021/030468; mailed Nov. 16, 2021.

(Continued)

*Primary Examiner* — Hoon K Song
(74) *Attorney, Agent, or Firm* — Studebaker Brackett PLLC

(57) ABSTRACT

A control apparatus including at least one processor that is configured to: capture a low-energy image by a radiography apparatus by emitting radiation having first energy to a subject into which a contrast medium has been injected, and then sequentially acquires each of a plurality of high-energy images captured by the radiography apparatus at different timings by emitting radiation having second energy higher than the first energy to the subject into which the contrast medium has been injected, sequentially derive a body movement amount of the subject from each of the plurality of high-energy images, and perform, in a case in which the derived body movement amount exceeds a threshold value, control of causing the radiography apparatus to re-capture the low-energy image before a next high-energy image is captured.

18 Claims, 16 Drawing Sheets

(51) Int. Cl.
*G06T 5/50* (2006.01)
*G06T 7/33* (2017.01)
*G06V 10/25* (2022.01)
*G06V 40/20* (2022.01)

(52) U.S. Cl.
CPC .................. *G06T 5/50* (2013.01); *G06T 7/33* (2017.01); *G06V 10/25* (2022.01); *G06V 40/20* (2022.01); *G06T 2207/20224* (2013.01)

(56) References Cited

U.S. PATENT DOCUMENTS

| | | | |
|---|---|---|---|
| 2013/0077845 A1* | 3/2013 | Flohr | A61B 6/463 382/131 |
| 2016/0007943 A1 | 1/2016 | Hoernig | |
| 2017/0119336 A1 | 5/2017 | Jacob et al. | |
| 2017/0150936 A1 | 6/2017 | Yoda | |
| 2017/0231593 A1 | 8/2017 | Fukuda et al. | |
| 2018/0360403 A1* | 12/2018 | Muller | A61B 6/06 |
| 2019/0388051 A1 | 12/2019 | Morita et al. | |
| 2022/0183648 A1* | 6/2022 | Abe | A61B 6/467 |

OTHER PUBLICATIONS

International Preliminary Report On Patentability (Chapter I) and Written Opinion of the International Searching Authority issued in PCT/JP2021/030468; issued Mar. 28, 2023.

The extended European search report issued by the European Patent Office on Jul. 17, 2023, which corresponds to European 21872043. 1-1126 and is related to U.S. Appl. No. 18/177,015.

* cited by examiner

FIG. 2
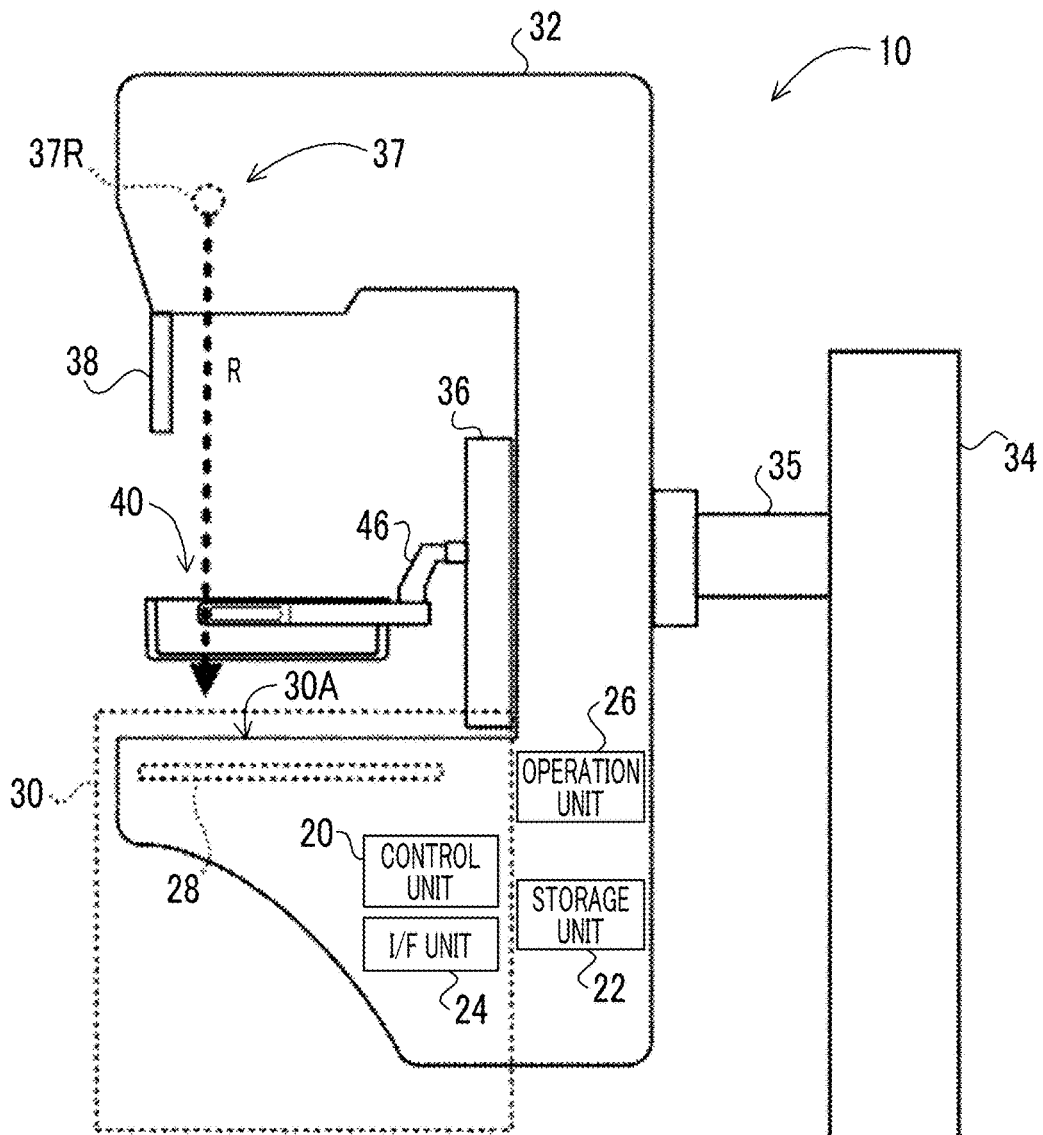
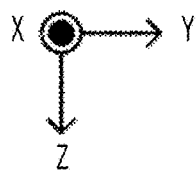

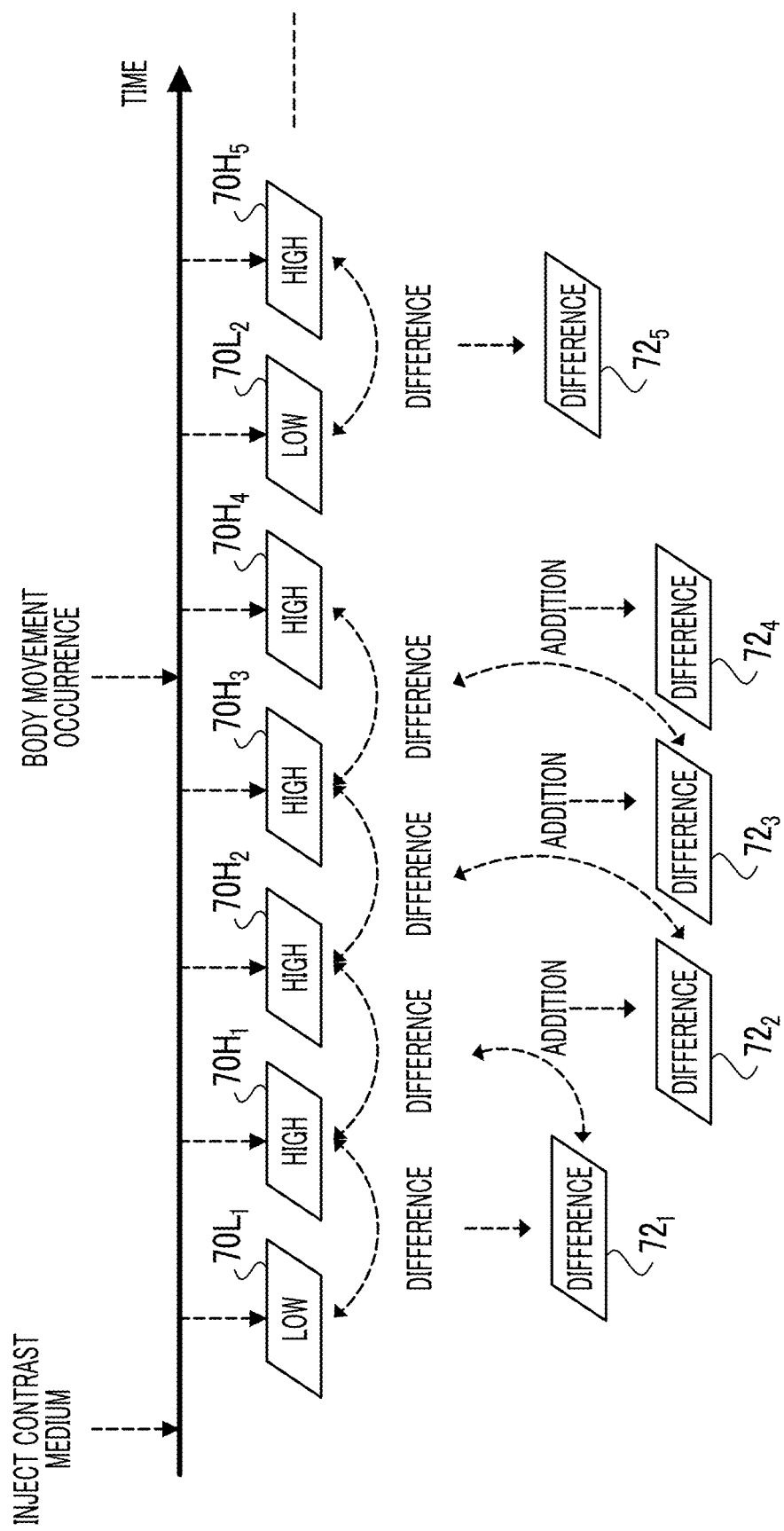

CONTROL APPARATUS, CONTROL METHOD, AND CONTROL PROGRAM

CROSS-REFERENCE TO RELATED APPLICATIONS

This application is a continuation application of International Application No. PCT/JP2021/030468, filed on Aug. 19, 2021, which is incorporated herein by reference in its entirety. Further, this application claims priority from Japanese Patent Application No. 2020-162695, filed on Sep. 28, 2020, the disclosure of which is incorporated by reference herein in their entirety.

BACKGROUND

Technical Field

The present disclosure relates to a control apparatus, a control method, and a non-transitory storage medium storing a control program.

Related Art

A technology of performing contrast imaging of capturing a low-energy image and a high-energy image by irradiating a subject into which a contrast medium has been injected with radiation having different energies and generating a difference image showing a difference between the high-energy image and the low-energy image to generate a radiation image in which the contrast medium is enhanced is known. As a technology of generating a difference image showing a difference between a low-energy image and a high-energy image, for example, a technology disclosed in JP2017-104531A is known. In the technology disclosed in JP2017-104531A, a technology is described in which, in X-ray computed tomography (CT) apparatus, a projection image, which is the low-energy image, is reconstructed, a projection image, which is the high-energy image, is reconstructed, and a difference image of a reconstructed image is generated.

By the way, in diagnosing a lesion or the like in a subject, it is desired to observe a temporal change of a contrast medium permeating a region of interest, such as a lesion, specifically, a temporal change of a contrast amount. In a case of observing the temporal change of the contrast amount, since the imaging time is long, a body movement of the subject may occur during the imaging. The technology disclosed in JP2017-104531A may be influenced by the body movement of the subject. For example, in a case in which a body movement amount of the subject is relatively large, the influence of the body movement of the subject may appear in the difference image.

SUMMARY

The present disclosure is made in view of the above circumstances, and provides a control apparatus, a control method, and a non-transitory storage medium storing a control program capable of reducing an influence of a body movement of a subject in contrast imaging for observing a temporal change of a contrast amount.

A first aspect of the present disclosure relates to a control apparatus comprising at least one processor, in which the processor acquires a low-energy image captured by a radiography apparatus by emitting radiation having first energy to a subject into which a contrast medium has been injected, sequentially acquires each of a plurality of high-energy images captured by the radiography apparatus at different timings by emitting radiation having second energy higher than the first energy to the subject into which the contrast medium has been injected, sequentially derives a body movement amount of the subject from each of the plurality of high-energy images, performs, in a case in which the derived body movement amount exceeds a threshold value, control of causing the radiography apparatus to re-capture the low-energy image before a next high-energy image is captured, and generates a plurality of difference images showing a difference between the low-energy image and each of the plurality of high-energy images.

A second aspect of the present disclosure relates to the control apparatus according to the first aspect, in which the processor generates a difference image showing a difference from the low-energy image captured at a timing closest to an imaging timing of the high-energy image.

A third aspect of the present disclosure relates to the control apparatus according to the first aspect, in which the processor generates a difference image showing a difference from the re-captured low-energy image from a high-energy image in which the derived body movement amount exceeds the threshold value.

A fourth aspect of the present disclosure relates to the control apparatus according to the first aspect, in which the processor switches the low-energy image to be used for generating the difference image with a timing at which a body movement of the subject has occurred as reference.

A fifth aspect of the present disclosure relates to the control apparatus according to the first aspect, in which the processor generates a first difference image showing a difference from a high-energy image having an imaging timing closest to an imaging timing of the low-energy image, generates a second difference image showing a difference between the high-energy images, and generates the plurality of difference images by using the first difference image and the second difference image.

A sixth aspect of the present disclosure relates to the control apparatus according to any one of the first to fifth aspects, in which the processor generates a difference image for body movement analysis showing a difference between two continuously captured high-energy images among the plurality of high-energy images, and sequentially derives the body movement amount of the subject from the generated difference image for body movement analysis.

A seventh aspect of the present disclosure relates to the control apparatus according to any one of the first to fifth aspects, in which the processor sequentially derives the body movement amount of the subject from each of the plurality of high-energy images with the low-energy image as a reference.

An eighth aspect of the present disclosure relates to the control apparatus according to any one of the first to seventh aspects, in which the processor generates the plurality of difference images after performing registration between the low-energy image and each of the plurality of high-energy images.

A ninth aspect of the present disclosure relates to the control apparatus according to the eighth aspect, in which the processor performs registration between a region of interest in the low-energy image and a region of interest in each of the plurality of high-energy images.

A tenth aspect of the present disclosure relates to the control apparatus according to any one of the first to seventh aspects, in which the processor corrects each of the plurality of high-energy images according to the body movement amount, and generates a plurality of difference images showing a difference between the low-energy image and each of the corrected plurality of high-energy images.

An eleventh aspect of the present disclosure relates to the control apparatus according to any one of the first to tenth aspects, in which the processor gives a notification that a body movement has occurred in a case in which the derived body movement amount exceeds the threshold value.

A twelfth aspect of the present disclosure relates to the control apparatus according to any one of the first to eleventh aspects, in which the processor continuously displays the plurality of difference images as a moving image in a time series order of capturing.

A thirteenth aspect of the present disclosure relates to the control apparatus according to any one of the first to eleventh aspects, in which the processor displays a difference image having a highest contrast of a region of interest among the plurality of difference images.

A fourteenth aspect of the present disclosure relates to the control apparatus according to any one of the first to thirteenth aspects, in which the processor derives a contrast amount of a region of interest in each of the plurality of difference images, and generates information indicating a temporal change of the contrast amount of the region of interest and displays the generated information.

A fifteenth aspect of the present disclosure relates to the control apparatus according to any one of the first to fourteenth aspects, in which the subject is a breast, and the radiography apparatus is a mammography apparatus.

In addition, a sixteenth aspect of the present disclosure relates to a control apparatus comprising at least one processor, in which the processor captures a low-energy image by a radiography apparatus by emitting radiation having first energy to a subject into which a contrast medium has been injected, and then sequentially acquires each of a plurality of high-energy images captured by the radiography apparatus at different timings by emitting radiation having second energy higher than the first energy to the subject into which the contrast medium has been injected, sequentially derives a body movement amount of the subject from each of the plurality of high-energy images, and performs, in a case in which the derived body movement amount exceeds a threshold value, control of causing the radiography apparatus to re-capture the low-energy image before a next high-energy image is captured.

In addition, a seventeenth aspect of the present disclosure relates to a control method executed by a computer, the method comprising acquiring a low-energy image captured by a radiography apparatus by emitting radiation having first energy to a subject into which a contrast medium has been injected, sequentially acquiring each of a plurality of high-energy images captured by the radiography apparatus at different timings by emitting radiation having second energy higher than the first energy to the subject into which the contrast medium has been injected, sequentially deriving a body movement amount of the subject from each of the plurality of high-energy images, performing, in a case in which the derived body movement amount exceeds a threshold value, control of causing the radiography apparatus to re-capture the low-energy image before a next high-energy image is captured, and generating a plurality of difference images showing a difference between the low-energy image and each of the plurality of high-energy images.

In addition, in order to achieve the objects, an eighteenth aspect of the present disclosure relates to a non-transitory storage medium storing a control program causing a computer to execute a control processing, the control processing comprising: acquiring a low-energy image captured by a radiography apparatus by emitting radiation having first energy to a subject into which a contrast medium has been injected, sequentially acquiring each of a plurality of high-energy images captured by the radiography apparatus at different timings by emitting radiation having second energy higher than the first energy to the subject into which the contrast medium has been injected, sequentially deriving a body movement amount of the subject from each of the plurality of high-energy images, performing, in a case in which the derived body movement amount exceeds a threshold value, control of causing the radiography apparatus to re-capture the low-energy image before a next high-energy image is captured, and generating a plurality of difference images showing a difference between the low-energy image and each of the plurality of high-energy images.

According to the present disclosure, it is possible to reduce the influence of the body movement of the subject in the contrast imaging for observing the temporal change of the contrast amount.

BRIEF DESCRIPTION OF THE DRAWINGS

FIG. 2 is a side view showing an example of an appearance of a mammography apparatus according to the embodiment.

FIG. 7B is a diagram for describing another example of the generation method of the difference image.

DETAILED DESCRIPTION

In the following, an embodiment of the present invention will be described in detail with reference to the drawings. It should be noted that the present embodiment does not limit the present invention.

Figure 1:
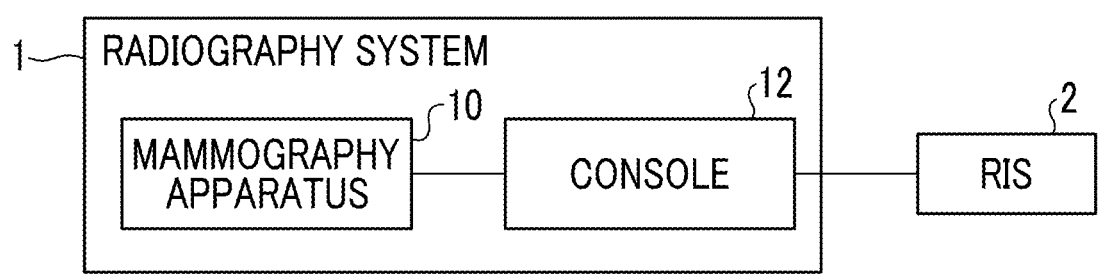
FIG. 1 is a configuration diagram schematically showing an example of an overall configuration of a radiography system according to an embodiment.

First, an example of an overall configuration of a radiography system according to the present embodiment will be described. FIG. 1 shows a configuration diagram showing an example of an overall configuration of a radiography system 1 according to the present embodiment. As shown in FIG. 1, the radiography system 1 according to the present embodiment comprises a mammography apparatus 10 and a console 12. The mammography apparatus 10 according to the present embodiment is an example of a radiography apparatus according to the present disclosure. In addition, the console 12 according to the present embodiment is an example of a control apparatus according to the present disclosure.

First, the mammography apparatus 10 according to the present embodiment will be described. FIG. 2 shows a side view showing an example of an appearance of the mammography apparatus 10 according to the present embodiment. It should be noted that FIG. 2 shows the example of the appearance of the mammography apparatus 10 as viewed from a right side of an examinee.

The mammography apparatus 10 according to the present embodiment is an apparatus that uses a breast of the examinee as a subject and captures a radiation image of the breast by irradiating the breast with radiation R (for example, X-rays). It should be noted that the mammography apparatus 10 may be an apparatus that images the breast of the examinee in a state in which the examinee is sitting on a chair (including a wheelchair) or the like (sitting state) in addition to a state in which the examinee is standing (standing state).

In addition, the mammography apparatus 10 according to the present embodiment has a function of performing two types of imaging of so-called contrast imaging in which the imaging is performed in a state in which a contrast medium has been injected into the breast of the examinee and general imaging. It should be noted that, in the present embodiment, the imaging to be performed in a state in which the contrast medium has been injected into the breast of the examinee refers to the "contrast imaging", and the imaging that is not the contrast imaging refers to the "general imaging".

In the mammography apparatus 10, in a case of performing the contrast imaging, the radiation image is captured by emitting the radiation having the first energy from the radiation source 37R to the breast in a state in which the contrast medium has been injected. In addition, in the mammography apparatus 10, the radiation image is captured by emitting the radiation having the second energy higher than the first energy from the radiation source 37R to the breast in a state in which the contrast medium has been injected. It should be noted that, in the present embodiment, the radiation image captured by emitting the radiation R having the first energy is referred to as a "low-energy image", and the radiation image captured by emitting the radiation R having the second energy is referred to as a "high-energy image". In addition, in a case in which the images captured by the mammography apparatus 10 are collectively referred to without distinction between types, such as the low-energy image and the high-energy image, the images are simply referred to as the "radiation image".

As shown in FIG. 2, the mammography apparatus 10 according to the present embodiment comprises a control unit 20, a storage unit 22, and an interface (I/F) unit 24 inside the imaging table 30. The control unit 20 controls an overall operation of the mammography apparatus 10 under the control of the console 12. The control unit 20 comprises a central processing unit (CPU), a read only memory (ROM), and a random access memory (RAM) (all not shown). The ROM stores, in advance, various programs, including an imaging processing program for performing control related to radiation image capturing, which is executed by the CPU. The RAM transitorily stores various data.

The storage unit 22 stores the image data of the radiation image captured by the radiation detector 28 or various types of other information. Specific examples of the storage unit 22 include a hard disk drive (HDD) and a solid state drive (SSD). The I/F unit 24 performs communication of various types of information with the console 12 by wireless communication or wired communication. The image data of the radiation image captured by the radiation detector 28 in the mammography apparatus 10 is transmitted to the console 12 via the I/F unit 24 by wireless communication or wired communication.

In addition, an operation unit 26 is provided as a plurality of switches on an imaging table 30 of the mammography apparatus 10, for example. It should be noted that the operation unit 26 may be provided as a touch panel type switch, or may be provided as a foot switch operated by a user, such as a doctor or an engineer with a foot.

The radiation detector 28 detects the radiation R that has passed through the breast which is the subject. In addition, as shown in FIG. 2, the radiation detector 28 is disposed inside the imaging table 30. In the mammography apparatus 10 according to the present embodiment, the user positions the breast of the examinee on an imaging surface 30A of the imaging table 30 in a case of performing the imaging.

The radiation detector 28 detects the radiation R transmitted through the breast of the examinee and the imaging table 30, generates a radiation image based on the detected radiation R, and outputs image data representing the generated radiation image. A type of the radiation detector 28 according to the present embodiment is not particularly limited. For example, a radiation detector of an indirect conversion method that converts the radiation R into light and converts the converted light into a charge may be used, and a radiation detector of a direct conversion method that directly converts the radiation R into a charge may be used.

A radiation emitting unit 37 comprises the radiation source 37R. As shown in FIG. 2, the radiation emitting unit 37 is provided in an arm part 32 together with the imaging table 30 and the compression unit 36. As shown in FIG. 2, a face guard 38 is attachable and detachable at a position near the examinee on the arm part 32 below the radiation emitting unit 37. The face guard 38 is a protective member for protecting the examinee from the radiation R emitted from the radiation source 37R.

It should be noted that, as shown in FIG. 2, the mammography apparatus 10 according to the present embodiment comprises the arm part 32, a base 34, and a shaft part 35. The arm part 32 is held by the base 34 to be movable in a vertical direction (Z-axis direction). The shaft part 35 connects the arm part 32 to the base 34. In addition, the arm part 32 is rotatable relative to the base 34 with the shaft part 35 as a rotation axis.

The arm part 32, the imaging table 30, and the compression unit 36 can be separately rotated relative to the base 34 with the shaft part 35 as a rotation axis. In the present embodiment, the base 34, the arm part 32, the imaging table 30, and the compression unit 36 are each provided with an engaging part (not shown), and each of the arm part 32, the imaging table 30, and the compression unit 36 is connected to the base 34 by switching a state of the engaging part. One or two of the arm part 32, the imaging table 30, or the compression unit 36, which are connected to the shaft part 35, are integrally rotated around the shaft part 35.

The compression unit 36 is provided with a compression plate driving unit (not shown) that moves the compression plate 40 in the vertical direction (Z-axis direction). The compression plate 40 according to the present embodiment has a function of compressing the breast of the examinee. A support part 46 of the compression plate 40 is attachably and detachably attached to the compression plate driving unit, is moved in the vertical direction (Z-axis direction) by the compression plate driving unit, and compresses the breast of the examinee with the imaging table 30.

On the other hand, the console 12 according to the present embodiment has a function of controlling the mammography apparatus 10 by using an imaging order and various types of information acquired from a radiology information system (RIS) 2 via a wireless communication local area network (LAN) and the like, and an instruction performed by the user by an operation unit 56 and the like.

Figure 3:
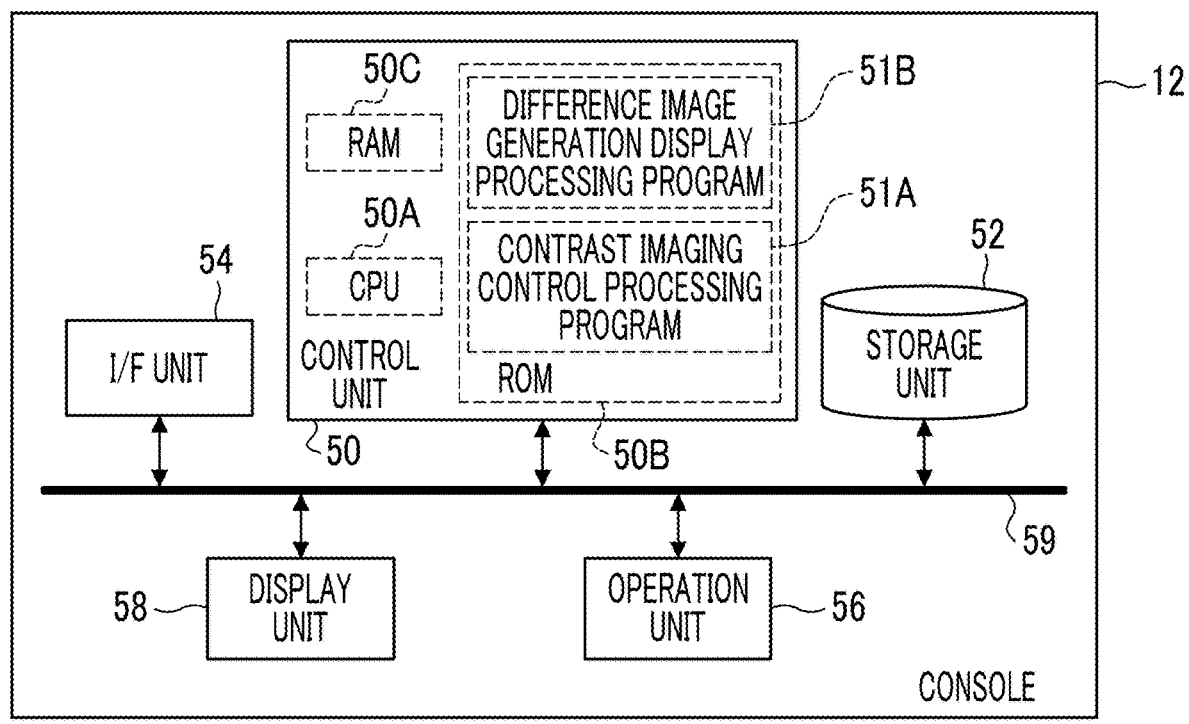
FIG. 3 is a block diagram showing an example of a configuration of a console according to the embodiment.

The console 12 according to the present embodiment is, for example, a server computer. As shown in FIG. 3, the console 12 comprises a control unit 50, a storage unit 52, an I/F unit 54, the operation unit 56, and a display unit 58. The control unit 50, the storage unit 52, the I/F unit 54, the operation unit 56, and the display unit 58 are connected to each other via a bus 59, such as a system bus or a control bus, such that various types of information can be exchanged.

The control unit 50 according to the present embodiment controls an overall operation of the console 12. The control unit 50 comprises a CPU 50A, a ROM 50B, and a RAM 50C. The ROM 50B stores, in advance, various programs including a contrast imaging control processing program 51A and a difference image generation display processing program 51B, which are executed by the CPU 50A and will be described below. The RAM 50C transitorily stores various data. The CPU 50A according to the present embodiment is an example of a processor according to the present disclosure. The contrast imaging control processing program 51A and the difference image generation display processing program 51B according to the present embodiment are examples of a control program according to the present disclosure.

The storage unit 52 stores the image data of the radiation image captured by the mammography apparatus 10 or various types of other information. Specific examples of the storage unit 52 include an HDD and an SSD.

The operation unit 56 is used by the user to input the instruction, various types of information, and the like related to the radiation image capturing and the like, including an irradiation instruction of the radiation R. The operation unit 56 is not particularly limited, and examples thereof include various switches, a touch panel, a touch pen, and a mouse. The display unit 58 displays various types of information. It should be noted that the operation unit 56 and the display unit 58 may be integrated to form a touch panel display.

The I/F unit 54 performs communication of various types of information between the mammography apparatus 10 and the RIS 2 by wireless communication or wired communication. The console 12 according to the present embodiment receives the image data of the radiation image captured by the mammography apparatus 10 from the mammography apparatus 10 via the I/F unit 54 by wireless communication or wired communication.

Figure 4:
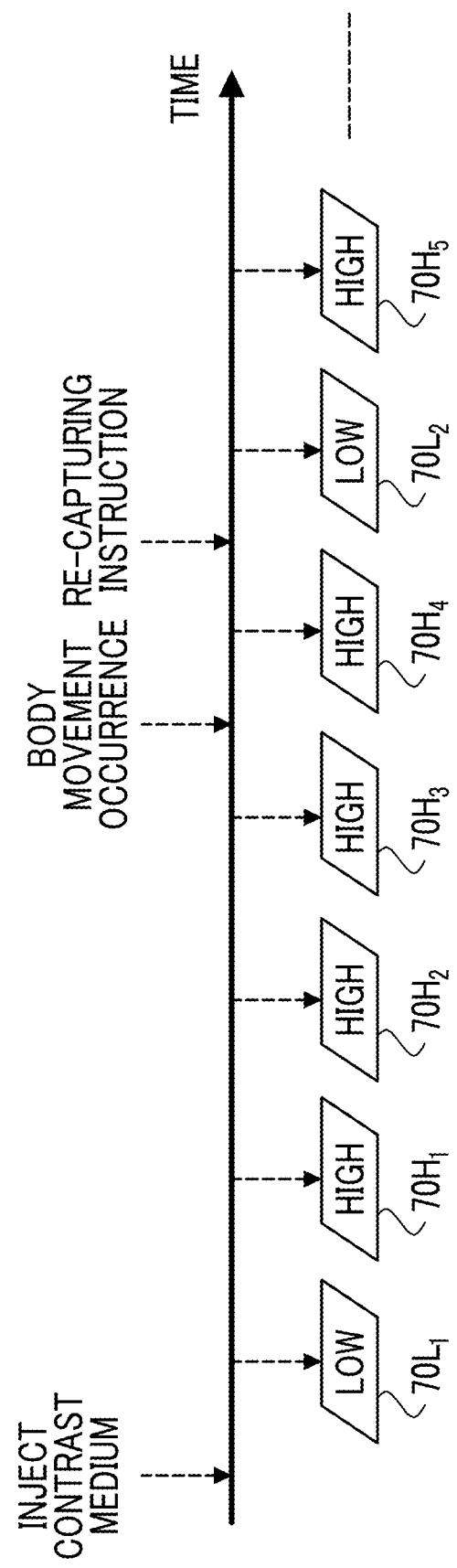
FIG. 4 is a time chart showing an example of imaging timings of a low-energy image and a high-energy image in contrast imaging using the mammography apparatus according to the embodiment.

Further, a functional configuration of the console 12 according to the present embodiment will be described with reference to FIGS. 4 and 5. FIG. 4 shows an example of imaging timings of a low-energy image 70L and a high-energy image 70H in contrast imaging by the mammography apparatus 10 according to the present embodiment. In the example shown in FIG. 4, in a case in which the contrast imaging is started, first, a low-energy image 70L (see FIG. 4, $70L_1$) is captured, and then high-energy images 70H (see FIG. 4, $70H_1$ to $70H_4$) are captured each time the predetermined time elapses. Then, in a case in which a body movement of the breast is detected, the low-energy image 70L (see FIG. 4, $70L_2$) is re-captured, and then the high-energy image 70H (see FIG. 4, $70H_5$) is imaged each time a predetermined time elapses. In this way, the low-energy image 70L and the high-energy image 70H are repeatedly captured until a contrast imaging time ends.

Figure 5:
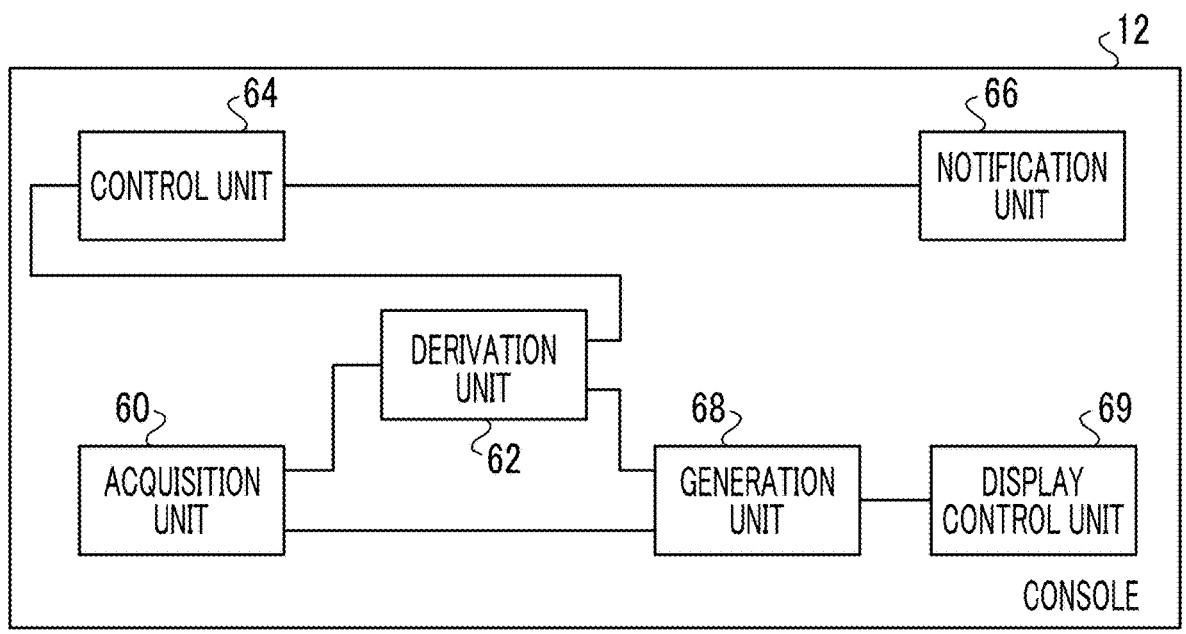
FIG. 5 is a functional block diagram showing an example of a function of the console according to the embodiment.

Further, FIG. 5 shows a functional block diagram of an example of the configuration of the console 12 according to the present embodiment. As shown in FIG. 5, the console 12 comprises an acquisition unit 60, a derivation unit 62, a control unit 64, and a notification unit 66. As an example, in the console 12 according to the present embodiment, the CPU 50A of the control unit 50 also functions as the acquisition unit 60, the derivation unit 62, the control unit 64, and the notification unit 66 by the CPU 50A executing the contrast imaging control processing program 51A stored in the ROM 50B.

The acquisition unit 60 has a function of acquiring the low-energy image 70L and the high-energy image 70H captured by the mammography apparatus 10. Specifically, the acquisition unit 60 acquires image data representing the low-energy image 70L and image data representing the high-energy image 70H captured by the radiation detector 28 of the mammography apparatus 10 via the I/F unit 24 and the I/F unit 54. The acquisition unit 60 outputs the acquired low-energy image 70L and high-energy image 70H to the derivation unit 62 and the generation unit 68.

The derivation unit 62 has a function of deriving an amount of the body movement of the breast (hereinafter, referred to as "body movement amount") from each of the plurality of high-energy images 70H. The body movement of the breast includes a case in which a body tissue, such as a mammary gland structure, in the breast is moved and a case in which the breast is moved as a whole due to the body movement of the examinee. As the breast is thicker, the mammary gland structure tends to be likely to be moved with the temporal change even in a compression state. Therefore, as the breast is thicker, the body movement is likely to occur. In addition, since the breast is softer as a proportion of fat is increased as the composition of the breast, the mammary gland structure tends to be likely to be moved with the temporal change even in the compression state. Therefore, as the proportion of fat in the breast is higher or as the breast is softer, the body movement tends to be likely to occur. In addition, as the subject gets older, it is difficult for the subject to maintain the same posture, so that the subject itself tends to be likely to be moved. Therefore, as the subject gets older, the body movement tends to be likely to occur. The derivation unit 62 according to the present embodiment derives the body movement amount of the breast that has occurred in this way. The derivation unit 62 outputs the derived body movement amount of the breast to the control unit 64 and the generation unit 68.

Figure 6:
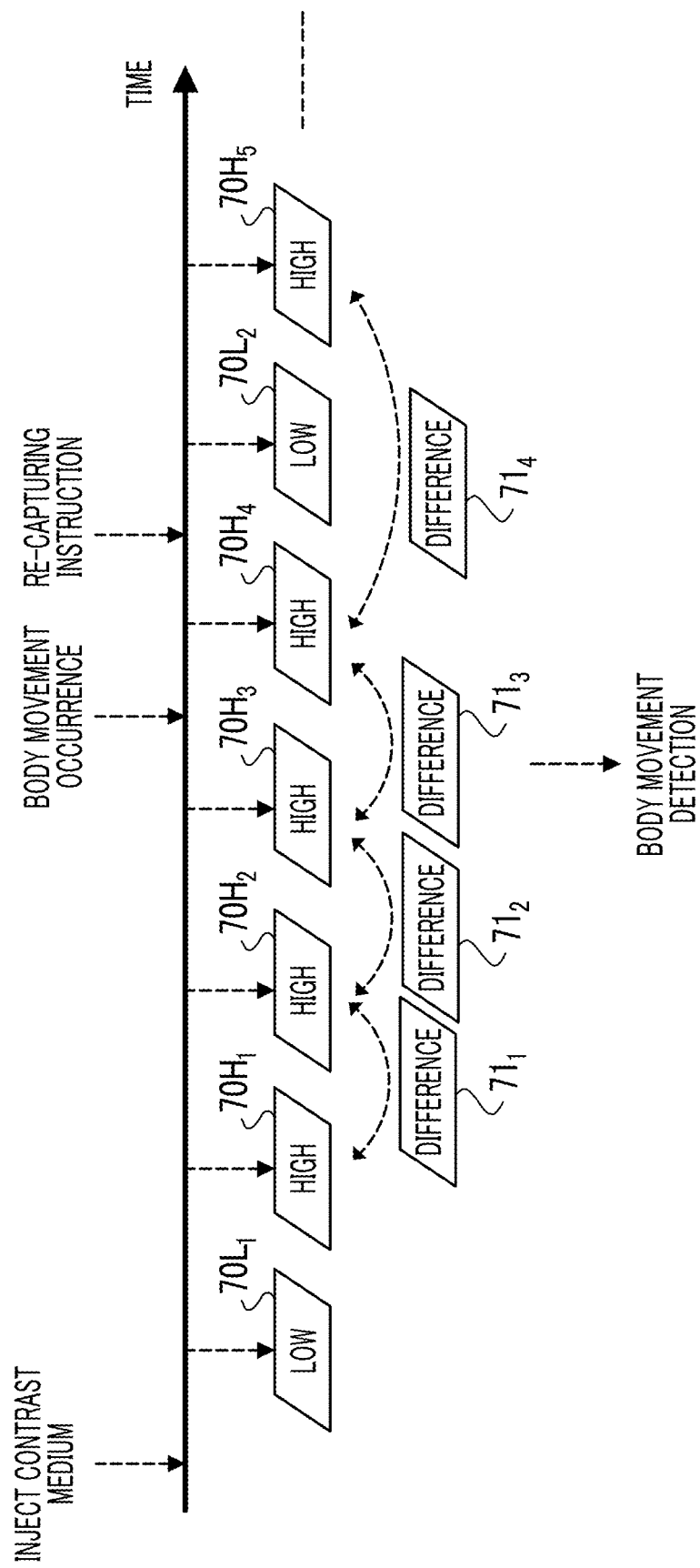
FIG. 6 is a diagram showing an example of a derivation method of a body movement amount of a breast.

As shown in FIG. 6 as an example, the derivation unit 62 according to the present embodiment generates a difference image for body movement analysis 71 (see FIGS. 6, 711 to 714) showing a difference between the high-energy images 70H (see FIG. 6, $70H_1$ to $70H_5$) which are continuous in time series, and derives the body movement amount based on the generated difference image for body movement analysis 71.

Specifically, the derivation unit 62 generates the difference image for body movement analysis 711 showing the difference between the high-energy image $70H_1$ and the high-energy image $70H_2$. More specifically, the derivation unit 62 generates the difference image data for body movement analysis representing the difference image for body movement analysis 711 by subtracting the image data of the high-energy image $70H_1$ from the image data of the high-energy image $70H_2$ for each corresponding pixel. In addition, the derivation unit 62 derives the body movement amount of the breast from the generated difference image for body movement analysis 711. Similarly, the derivation unit 62 generates a difference image for body movement analysis 712 showing the difference between the high-energy image $70H_2$ and the high-energy image $70H_3$, and derives the body movement amount of the breast from the generated difference image for body movement analysis 712. The derivation unit 62 generates the difference image for body movement analysis 713 showing the difference between the high-energy image $70H_3$ and the high-energy image $70H_4$, and derives the body movement amount of the breast from the generated difference image for body movement analysis 713. The derivation unit 62 generates the difference image for body movement analysis 714 showing the difference between the high-energy image $70H_4$ and the high-energy image $70H_5$, and derives the body movement amount of the breast from the generated difference image for body movement analysis 714.

It should be noted that, in the derivation unit 62 according to the present embodiment, an index value corresponding to the body movement amount and varying according to the body movement amount is derived as the body movement amount, instead of the actual body movement amount itself of the body movement of the breast. In addition, a method by which the derivation unit 62 derives the body movement amount of the breast from the difference image for body movement analysis 71 is not limited. For example, the difference image for body movement analysis 71 showing the difference between the high-energy images 70H before and after the body movement has occurred tends to have a greater pixel value than the difference image for body movement analysis 71 showing the difference between the high-energy images 70H in which the body movement does not occur. Therefore, the derivation unit 62 may derive a total value of the pixel values of the difference image for body movement analysis 71 as the body movement amount. In addition, for example, in the difference image for body movement analysis 71 showing the difference between the high-energy images 70H before and after the body movement has occurred, the body movement appears as a line, and thus the high-frequency component tends to be increased as compared with the difference image for body movement analysis 71 showing the difference between the high-energy images 70H in which the body movement does not occur. In addition, the image having the high-frequency component tends to be smaller influenced by the temporal change of the contrast amount than the image of the low-frequency component. Therefore, the derivation unit 62 may derive a total value of the pixel values of the image having the high-frequency component in the difference image for body movement analysis 71 as the body movement amount.

In addition, although the body movement amount of the breast that occurs during the imaging interval between the continuous high-energy images 70H is small, in a case in which the body movement is gradually performed over a long period of time, the body movement amount may be increased as a result. For example, in the example shown in FIG. 6, the body movement amount of the breast is small in a case in which the high-energy image $70H_1$ and the high-energy image $70H_2$ are compared, but the body movement amount of the breast may be large in a case in which the high-energy image $70H_1$ and the high-energy image $70H_3$ are compared. In such a case, it is preferable to adopt a form in which the body movement amount is derived based on the image obtained by adding the generated difference image for body movement analysis 71.

The control unit 64 has a function of controlling the contrast imaging. Specifically, the control unit 64 has a function of performing control related to the irradiation with the radiation R in the mammography apparatus 10 in the contrast imaging. More specifically, in the contrast imaging, the control unit 64 has a function of performing control of emitting the radiation R having the first energy from the radiation source 37R and control of emitting the radiation R having the second energy. In other words, the control unit 64 has a function of performing control of causing the mammography apparatus 10 to capture the low-energy image 70L and control of causing the mammography apparatus 10 to capture the high-energy image 70H.

For example, an iodine contrast medium with a k-absorption edge of 32 keV is generally used as the contrast medium for the contrast imaging. In the contrast imaging in this case, the low-energy image 70L is captured by emitting the radiation R having the first energy lower than the k-absorption edge of the iodine contrast medium. In addition, the high-energy image 70H is captured by emitting the radiation R having the second energy higher than the k-absorption edge of the iodine contrast medium.

A body tissue, such as a mammary gland, and the contrast medium have different absorption characteristics of the radiation. Therefore, in the high-energy image 70H captured as described above, the body tissue, such as the mammary gland or fat, is reflected, and the contrast medium is clearly reflected. In addition, in the low-energy image 70L, almost no contrast medium is reflected, and the body tissue, such as the mammary gland or fat, is clearly reflected. Therefore, a difference image 72 indicating a difference between the low-energy image 70L and the high-energy image 70H can be made to be an image in which a mammary gland structure is removed and the contrast medium is clearly reflected.

In addition, in the contrast imaging, as shown in FIG. 4, changes in a state in which the contrast medium permeates the breast are imaged in time series. For example, the contrast medium tends to more easily permeate in a lesion, such as a tumor, than the mammary gland. Also, as the lesion is more malignant, the contrast medium tends to permeate faster and the contrast medium tends to be washed out faster. Therefore, in the radiography system 1 according to the present embodiment, a temporal change or an amount of permeation (contrast amount) of the contrast medium permeating a region of interest, such as the lesion, is observed by using a plurality of difference images 72 obtained in time series.

In order to obtain the plurality of difference images 72, in the present embodiment, after the low-energy image 70L is captured, the high-energy image 70H is captured each time a predetermined time, such as 1 second, elapses. As described above, in order to observe the temporal change of the contrast amount of the region of interest, it is necessary to capture the high-energy image 70H in which the contrast medium is clearly reflected, according to the temporal change. On the other hand, the low-energy image 70L does not need to be captured as frequently as the high-energy image 70H because the temporal change of the state of the mammary gland structure, particularly, the temporal change of the imaging time of the contrast imaging is very small. However, in a case in which the body movement of the breast has occurred, an appropriate difference image 72 cannot be generated because, for example, the appearance of the mammary gland structure is different between the low-energy image 70L before the body movement and the high-energy image 70H after the body movement.

Therefore, the control unit 64 according to the present embodiment performs control of re-capturing the low-energy image 70L in a case in which the body movement amount of the breast derived by the derivation unit 62 exceeds a threshold value. For example, as described above, in a case in which the derivation unit 62 derives the total value of the pixel values of the difference image for body movement analysis 71 or the total value of the pixel values of the image having the high-frequency component in the difference image for body movement analysis 71 as the body movement amount, the control unit 64 performs control of re-capturing the low-energy image 70L in a case in which these pixel values exceed the threshold value. In this case, as the threshold value is, for example, a total value of the pixel values of the difference image for body movement analysis 71 between the high-energy images 70H before and after the body movement of the breast exceeding an allowable range has occurred, or a total value of the pixel values of the image having the high-frequency component of the difference image for body movement analysis 71 may be applied. It should be noted that, in this case, the allowable range of the body movement of the breast can be determined in consideration of, for example, an image quality of the difference image 72 showing the difference between the low-energy image 70L and the high-energy image 70H.

The notification unit 66 has a function of notifying the user that the body movement of the breast has occurred in a case in which the control unit 64 performs control of re-capturing the low-energy image 70L, in other words, in a case in which the body movement amount of the breast exceeds the threshold value. It should be noted that a notification method in which the notification unit 66 notifies that the body movement of the breast has occurred is not particularly limited, and for example, display may be performed by any of an audible display or a visible display.

In addition, the console 12 according to the present embodiment comprises the generation unit 68 and the display control unit 69. As an example, in the console 12 according to the present embodiment, the CPU 50A of the control unit 50 functions as the generation unit 68 and the display control unit 69 by the CPU 50A executing the difference image generation display processing program 51B stored in the ROM 50B.

The generation unit 68 has a function of generating the plurality of difference images 72 showing the difference between the low-energy image 70L and each of a plurality of high-energy images 70H. As an example, the generation unit 68 according to the present embodiment generates the difference image 72 between the low-energy image 70L and the plurality of high-energy images 70H captured in a period from capturing of a current low-energy image 70L to capturing of a next low-energy image 70L. The generation unit 68 generates the difference image 72 showing the difference between the re-captured low-energy image 70L and the high-energy image 70H in which the body movement amount derived by the derivation unit 62 exceeds the threshold value.

Figure 7A:
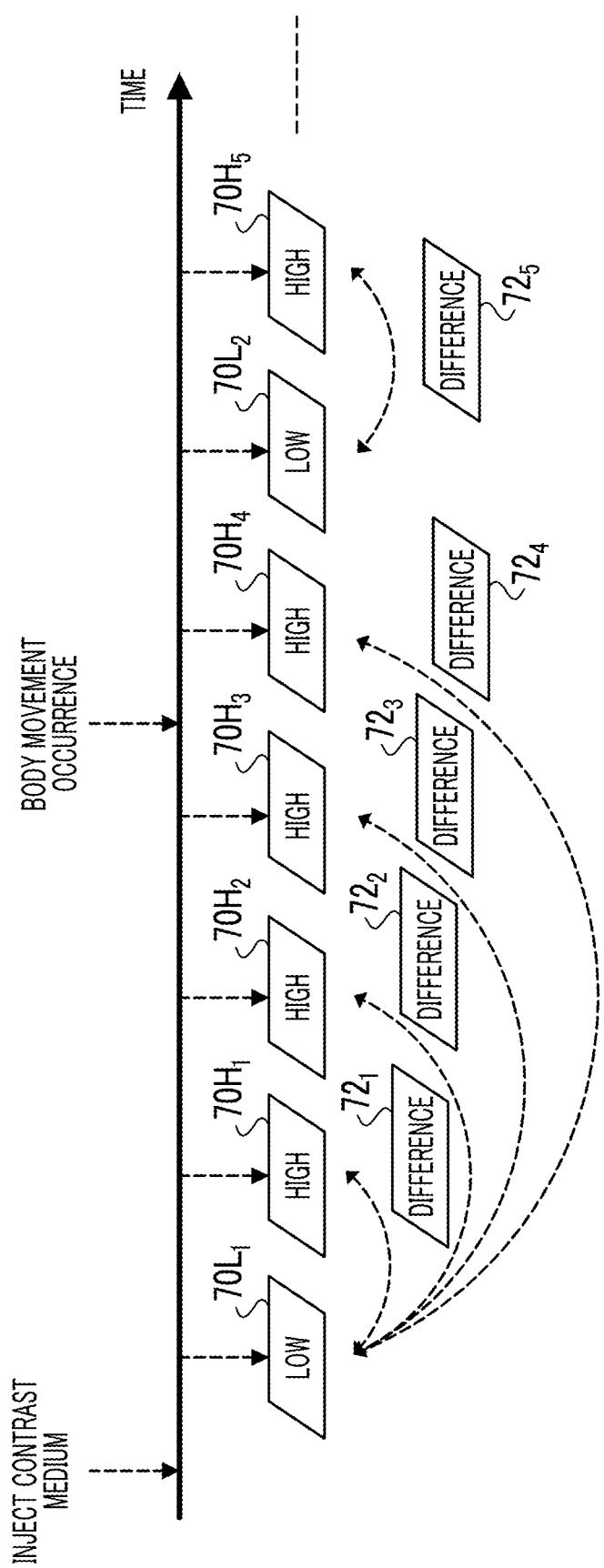
FIG. 7A is a diagram for describing an example of a generation method of a difference image.

As an example, in the present embodiment, the difference image 72 is generated by deriving the difference between the low-energy image 70L and each high-energy image 70H. Specifically, as shown in FIG. 7A, the generation unit 68 generates a difference image 721 between the low-energy image $70L_1$ and the high-energy image $70H_1$. Specifically, the generation unit 68 generates the difference image data representing the difference image 72 in which the mammary gland tissue is removed and the contrast medium is enhanced, by subtracting image data obtained by multiplying the low-energy image $70L_1$ by a predetermined coefficient from image data obtained by multiplying the high-energy image $70H_1$ by a predetermined coefficient for each corresponding pixel. Similarly, the generation unit 68 generates a difference image 722 between the low-energy image $70L_1$ and the high-energy image $70H_2$, generates a difference image 723 between the low-energy image $70L_1$ and the high-energy image $70H_3$, and generates a difference image 724 between the low-energy image $70L_1$ and the high-energy image $70H_4$. In addition, the generation unit 68 generates a difference image 725 between the low-energy image $70L_2$ and the high-energy image $70H_5$.

It should be noted that a method by which the generation unit 68 generates the difference image 72 is not limited to the method described above. For example, the difference image 72 may be generated by adding the difference between the high-energy images 70H to the difference between the low-energy image 70L and the high-energy image 70H. Specifically, as shown in FIG. 7B, as described above, the generation unit 68 generates the difference image 721 between the low-energy image $70L_1$ and the high-energy image $70H_1$. In addition, the generation unit 68 generates the difference image 722 by adding an image showing a difference between the high-energy image $70H_2$ and the high-energy image $70H_1$ to the difference image 721, generates the difference image 723 by adding an image showing a difference between the high-energy image $70H_3$ and the high-energy image $70H_2$ to the difference image 722, and generates the difference image 724 by adding an image showing a difference between the high-energy image $70H_4$ and the high-energy image $70H_3$ to the difference image 723.

It should be noted that the generation unit 68 according to the present embodiment performs registration between the low-energy image 70L and the high-energy image 70H before generating the difference image 72 showing the difference between the low-energy image 70L and the high-energy image 70H. For example, in a case in which the body movement of the breast has occurred even in a case in which the body movement amount is equal to or smaller than the threshold value, a position of a skin line or a position of a region of interest in the low-energy image 70L and a position of a skin line or a position of a region of interest in the high-energy image 70H are deviated. That is, the high-energy image 70H may be deviated according to the body movement amount of the breast. Therefore, it is preferable that the generation unit 68 generates the difference image 72 after correcting the deviation by performing registration between the low-energy image 70L and the high-energy image 70H. For example, it is preferable that the high-energy image 70H is corrected according to the body movement amount, and the difference image 72 showing the difference between the corrected high-energy image 70H and the low-energy image 70L is generated.

A specific method of performing registration between the low-energy image 70L and the high-energy image 70H by the generation unit 68 is not particularly limited, and the method need only be a method of associating portions (parts) that are considered to be anatomically the same and transforming the image into a state in which the corresponding portions overlap. For example, as in a known technology disclosed in JP2012-235807A, registration may be performed by moving a breast image showing the breast in parallel in a state in which the centroids of the mammary glands match and aligning the positions of the centroids. In addition, for example, as in a known technology disclosed in JP2010-188003A, linear registration may be performed by using an affine transformation or the like. In addition, for example, registration between the positions of the centroids of the breast region may be performed as in a known technology disclosed in JP2008-289698A.

It should be noted that, as registration performed by the generation unit 68, it is more preferable to perform registration between the position of the region of interest in the low-energy image 70L and the position of the region of interest in the high-energy image 70H. Therefore, the generation unit 68 according to the present embodiment performs registration between the position of the region of interest in the low-energy image 70L and the position of the region of interest in the high-energy image 70H. As an example, the generation unit 68 according to the present embodiment specifies the region of interest by applying computer aided diagnosis (CAD) to each of the low-energy image 70L and the high-energy image 70H. It should be noted that the method of specifying the region of interest is not limited to the present form, for example, the region of interest may be specified from each of the low-energy image 70L and the high-energy image 70H by displaying the low-energy image 70L and the high-energy image 70H on the display unit 58 and receiving the information about the region of interest designated by the user for each of the low-energy image 70L and the high-energy image 70H. It should be noted that the position or the shape of the region of interest that shifts to the radiation image may be changed before and after the body movement of the breast has occurred. Therefore, it is preferable to specify the region of interest for each of the captured low-energy image 70L and high-energy image 70H, in other words, for each of the captured radiation images. It should be noted that, in a case in which the user specifies the region of interest from the radiation image displayed on the display unit 58, it is relatively difficult for the user to designate the region of interest for each of the captured radiation images. In this case, the user may designate the region of interest for the radiation images before and after the body movement of the breast has occurred.

The display control unit 69 has a function of causing the display unit 58 to continuously display the difference images 72 generated by the generation unit 68 as a moving image in a time series order. In the present embodiment, the "moving image" means that still images are displayed one after another at high speed and recognized as the moving image. Therefore, the so-called "frame advance" is also included in the moving image depending on a degree of "high speed" in the display.

In addition, the display control unit 69 according to the present embodiment has a function of deriving each of information indicating the temporal change of the contrast amount of the region of interest in the difference image 72 and information indicating the temporal change of the contrast amount of an outside of the region of interest and displaying the derived information on the display unit 58. It should be noted that a method by which the display control unit 69 specifies the region of interest from the difference image is not particularly limited. For example, in a case in which the generation unit 68 specifies the region of interest, the display control unit 69 may specify the region of interest from the difference image 72 based on the position of the region of interest specified by the generation unit 68. In addition, for example, the region of interest may be specified from the difference image 72 by receiving information about the region of interest input by the user. Specifically, at least one image of the difference image 72, the low-energy image 70L, or the high-energy image 70H may be displayed on the display unit 58, and a region designated by the user operating the operation unit 56 on the display image may be received as the information about the region of interest. In addition, for example, the display control unit 69 may specify the region of interest by applying the CAD to the difference image 72. It should be noted that a method by which the display control unit 69 specifies the outside of the region of interest from the difference image 72 is not particularly limited. For example, a region excluding the region of interest from the region representing the breast in the difference image 72 may be specified as the outside of the region of interest. In addition, for example, a mammary gland region other than the region of interest may be specified as the outside of the region of interest.

In addition, the display control unit 69 according to the present embodiment has a function of displaying, on the display unit 58, information indicating a timing at which the body movement of the breast has occurred, more specifically, a timing at which the body movement amount of the breast derived by the derivation unit 62 exceeds the threshold value.

Next, an action of the console 12 in the contrast imaging by the radiography system 1 according to the present embodiment will be described with reference to the drawings.

Figure 8:
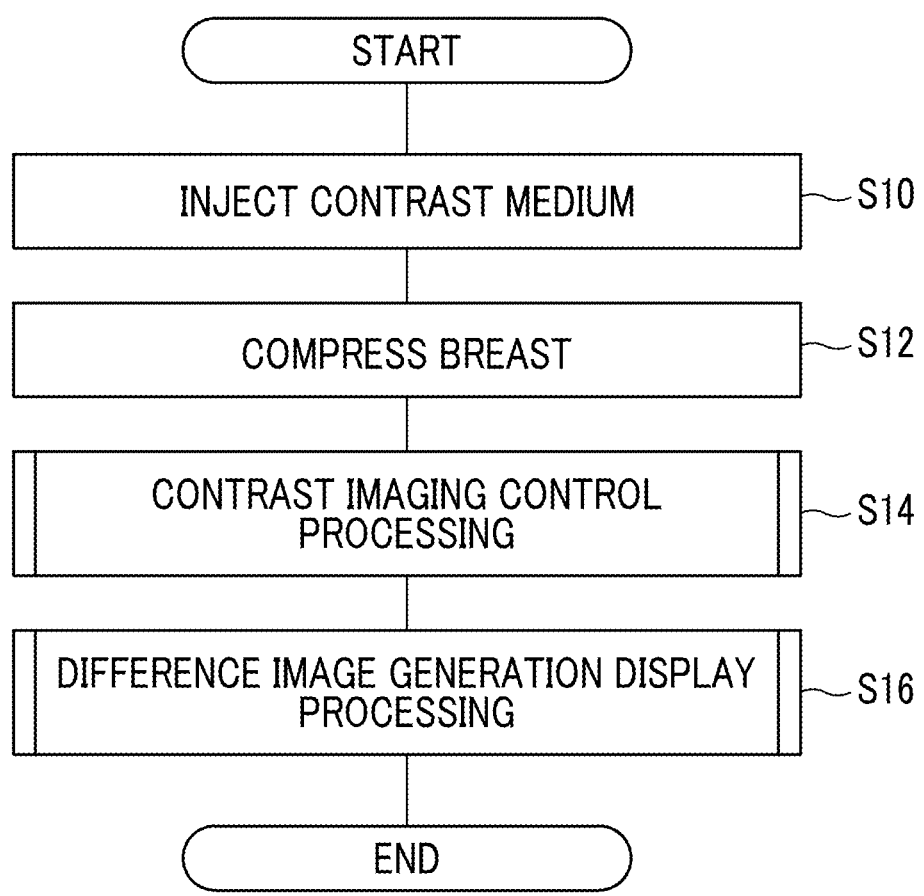
FIG. 8 is a flowchart showing an example of a flow of contrast imaging by the radiography system according to the embodiment.

FIG. 8 shows a flowchart showing an example of a flow of the contrast imaging by the radiography system 1 according to the present embodiment. In a case in which the contrast imaging is performed, first, the user injects the contrast medium into the breast, which is the subject, as shown in step S10 of FIG. 8. Next, as shown in step S12, the user positions the breast of the examinee on the imaging table 30 of the mammography apparatus 10 and compresses the breast with the compression plate 40.

Figure 9:
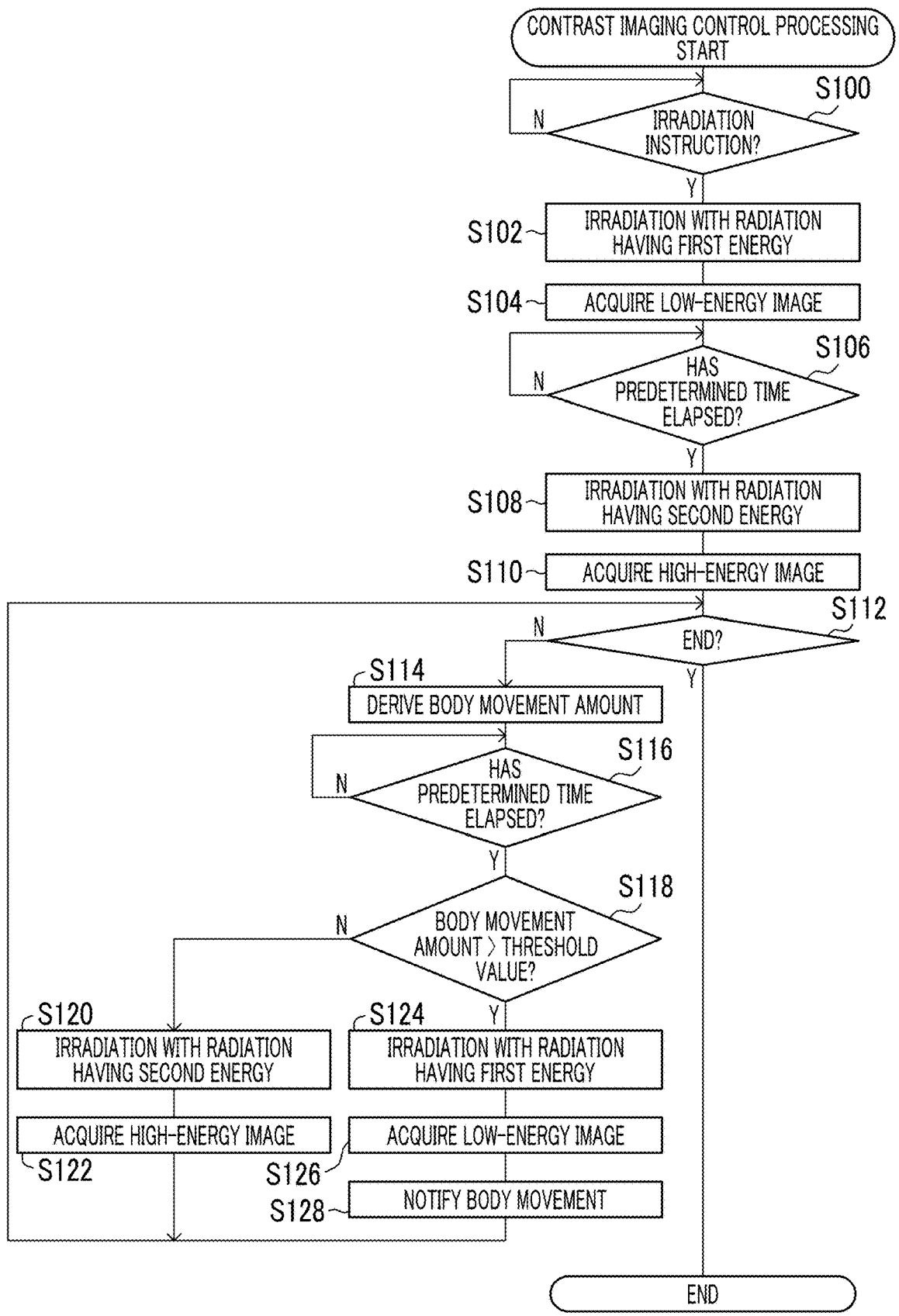
FIG. 9 is a flowchart showing an example of a flow of contrast imaging control processing executed in the console.

Next, in step S14, the contrast imaging control processing shown in FIG. 9 as an example is performed by the console 12 in order to perform the contrast imaging by the mammography apparatus 10. In the present embodiment, as described above, the control unit 64 of the console 12 performs control related to the irradiation with the radiation R in the mammography apparatus 10. In the console 12 according to the present embodiment, as an example, the CPU 50A of the control unit 50 executes the contrast imaging control processing program 51A stored in the ROM 50B, thereby executing the contrast imaging control processing shown in FIG. 9 as an example. FIG. 9 shows a flowchart showing an example of a flow of the contrast imaging control processing executed in the console 12 according to the present embodiment.

In step S100 of FIG. 9, the control unit 64 determines whether or not the irradiation instruction of the radiation R is received. A negative determination is made in the determination in step S100 until the irradiation instruction is received. On the other hand, in a case in which the irradiation instruction is received, a positive determination is made in the determination in step S100, and the processing proceeds to step S102.

In step S102, the control unit 64 outputs the instruction to perform the irradiation with the radiation R having the first energy to the mammography apparatus 10. In the mammography apparatus 10, the control unit 20 emits the radiation R having the first energy from the radiation source 37R toward the breast based on the instruction input from the console 12, and the low-energy image 70L is captured by the radiation detector 28.

In next step S104, the acquisition unit 60 acquires the low-energy image 70L from the mammography apparatus 10, as described above.

In next step S106, the control unit 64 determines whether or not a predetermined time has elapsed. A negative determination is made in the determination in step S106 until the predetermined time elapses. On the other hand, in a case in which the predetermined time has elapsed, a positive determination is made in the determination in step S106, and the processing proceeds to step S108.

In step S108, the control unit 64 outputs the instruction to perform the irradiation with the radiation R having the second energy to the mammography apparatus 10. In the mammography apparatus 10, the control unit 20 emits the radiation R having the second energy from the radiation source 37R toward the breast based on the instruction input from the console 12, and the high-energy image 70H is captured by the radiation detector 28.

In next step S110, the acquisition unit 60 acquires the high-energy image 70H from the mammography apparatus 10, as described above.

In step S112, the control unit 64 determines whether or not to end the present contrast imaging control processing. In a case in which a predetermined end condition is not satisfied, a negative determination is made in the determination in step S112, and the processing proceeds to step S114. The end condition may be, for example, a condition in which the processing ends in a case in which an elapsed time from the injection of the contrast medium into the breast has passed a time that is determined as the imaging time, in a case in which an elapsed time from the start of the irradiation with the radiation R has passed a time that is determined as a cumulative time of the irradiation time in the contrast imaging, in a case in which the number of times of capturing of the radiation image reaches a predetermined number of times, and in a case in which an instruction to end the imaging is received from the user.

In step S114, as described above, the derivation unit 62 derives the body movement amount of the breast from the high-energy image 70H. In the present embodiment, as described above, the derivation unit 62 generates the difference image for body movement analysis 71 showing the difference between the high-energy images 70H, and derives the body movement amount of the breast from the difference image for body movement analysis 71.

In next step S116, the control unit 64 determines whether or not the predetermined time has elapsed, as in step S106. A negative determination is made in the determination in step S116 until the predetermined time elapses. On the other hand, in a case in which the predetermined time has elapsed, a positive determination is made in the determination in step S116, and the processing proceeds to step S118.

In step S118, the control unit 64 determines whether or not the body movement amount of the breast derived in step S114 exceeds the threshold value (body movement amount>threshold value). In a case in which the body movement amount of the breast does not exceed the threshold value, in other words, in a case in which the body movement amount of the breast is equal to or smaller than the threshold value, a negative determination is made in the determination in step S118, and the processing proceeds to step S120.

It should be noted that, in a case of the high-energy image 70H (see FIG. 6, high-energy image $70H_1$) captured first after the start of the contrast imaging, the next high-energy image 70H (see FIG. 6, high-energy image $70H_2$) has not yet been captured. Therefore, it is not possible to generate the difference image for body movement analysis 71 showing the difference between the high-energy images 70H. Therefore, after the high-energy image 70H is acquired in step S110, in a case in which the processing after S120 has not been performed even once, the processing of step S114 is omitted, and in a case in which a positive determination is made in step S116, the processing of step S118 is omitted, and the processing proceeds to step S120.

In step S120, the control unit 64 outputs the instruction to perform the irradiation with the radiation R having the second energy to the mammography apparatus 10, as in step S108. In the mammography apparatus 10, the control unit 20 emits the radiation R having the second energy from the radiation source 37R toward the breast based on the instruction input from the console 12, and the high-energy image 70H is captured by the radiation detector 28.

In next step S122, the acquisition unit 60 acquires the high-energy image 70H from the mammography apparatus 10, as described above. In a case in which the processing of step S122 ends, the processing returns to step S112 and repeats the processing of steps S112 to S118 described above.

On the other hand, in step S118, in a case in which the body movement amount of the breast exceeds the threshold value, a positive determination is made, and the processing proceeds to step S124.

In step S124, the control unit 64 outputs the instruction to perform the irradiation with the radiation R having the first energy to the mammography apparatus 10, as in step S102. In the mammography apparatus 10, the control unit 20 emits the radiation R having the first energy from the radiation source 37R toward the breast to re-capture the low-energy image 70L (see FIG. 4, low-energy image $70L_2$) by the radiation detector 28 based on the instruction input from the console 12.

In next step S126, the acquisition unit 60 acquires the re-captured low-energy image 70L from the mammography apparatus 10, as described above.

In next step S128, the notification unit 66 notifies that the body movement of the breast has occurred. The notification unit 66 notifies that the body movement of the breast has occurred, so that the user confirms the state of the examinee, for example. As a result of the confirmation, for example, in a case in which the examinee is moved significantly, the user may give an instruction to stop the contrast imaging to the console 12 or the mammography apparatus 10. In a case in which the processing of step S128 ends, the processing returns to step S112 and repeats the processing of steps S112 to S118 described above.

On the other hand, in a case in which the end condition is satisfied in step S112, a positive determination is made in the determination, and the present contrast imaging control processing ends.

In a case in which the contrast imaging control processing shown in FIG. 9 ends in this way, the contrast imaging ends, and the processing of step S14 shown in FIG. 8 ends.

Figure 10:
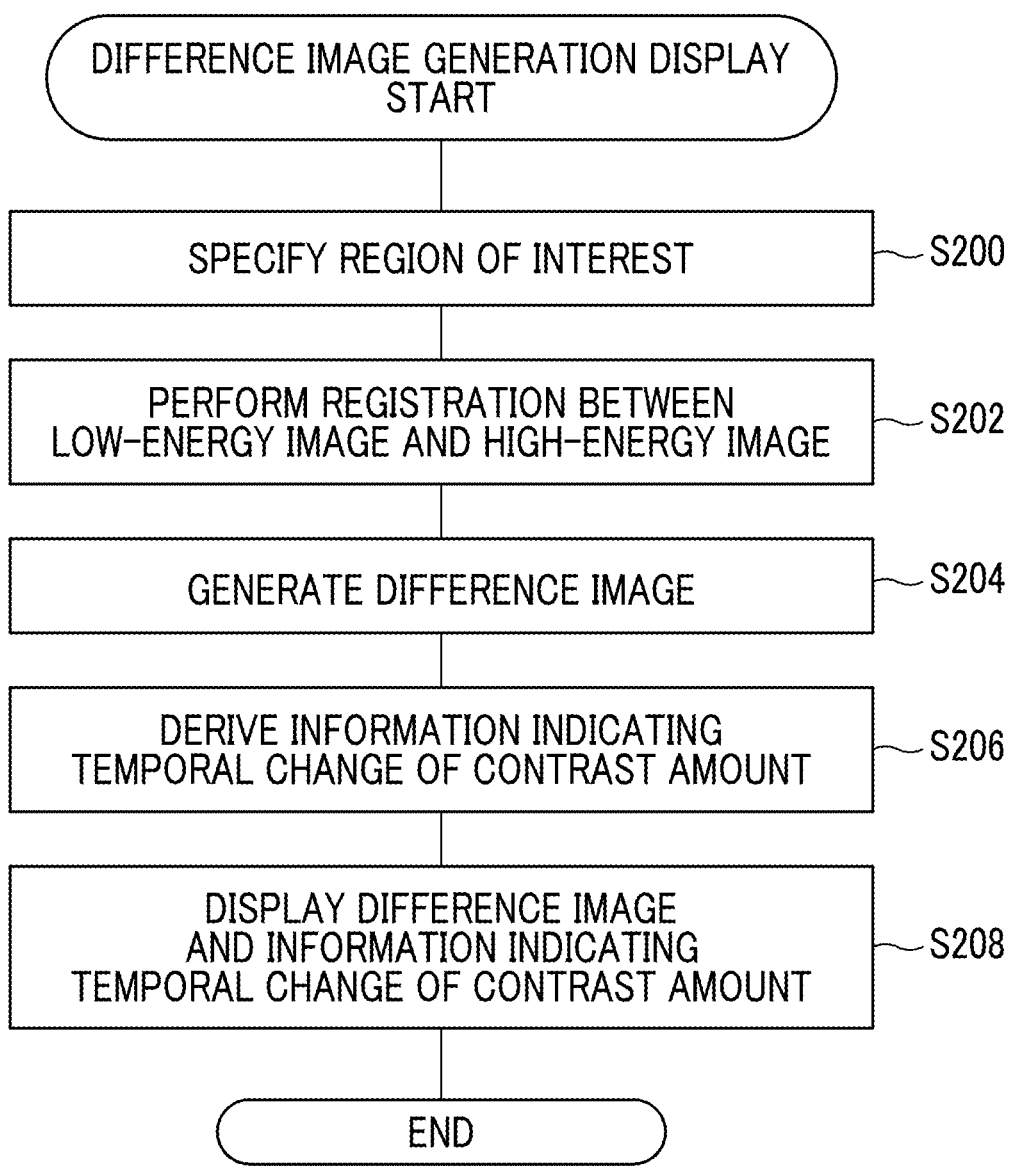
FIG. 10 is a flowchart showing an example of a flow of difference image generation display processing executed in the console.

In next step S16, the console 12 performs difference image generation display processing shown in FIG. 10. In the console 12 according to the present embodiment, as an example, the CPU 50A of the control unit 50 executes the difference image generation display processing program 51B stored in the ROM 50B, thereby executing the difference image generation display processing shown in FIG. 10 as an example. FIG. 10 shows a flowchart showing an example of a flow of the difference image generation display processing executed in the console 12 according to the present embodiment.

In step S200, the generation unit 68 specifies the region of interest from each of the low-energy image 70L and the high-energy image 70H acquired by the acquisition unit 60 from the mammography apparatus 10. Specifically, the generation unit 68 according to the present embodiment specifies the region of interest by applying the CAD to each of all the low-energy images 70L and the high-energy images 70H acquired by the acquisition unit 60.

In next step S202, the generation unit 68 performs registration between the low-energy image 70L and the high-energy image 70H, which are a combination for generating the difference image 72. As an example, as described above, the generation unit 68 according to the present embodiment performs registration between the position of the region of interest in the low-energy image 70L and the position of the region of interest in the high-energy image 70H.

In next step S204, as described above, the generation unit 68 generates the plurality of difference images 72 from all the low-energy images 70L and the high-energy images 70H acquired by the acquisition unit 60 from the mammography apparatus 10. In next step S204, the display control unit 69 specifies the region of interest from the difference image 72, as described above.

In next step S206, as described above, the display control unit 69 derives the information indicating the temporal change of the contrast amount. Specifically, the display control unit 69 derives the information indicating the temporal change of the contrast amount of the region of interest specified in step S200 in the difference image 72 generated in step S204. It should be noted that the display control unit 69 may not derive the contrast amount itself. For example, a brightness value of the pixel in the difference image 72 is changed according to the contrast amount. Therefore, the information indicating the temporal change of the brightness value of the difference image 72 may be used as the information indicating the temporal change of the contrast amount.

Figure 11:
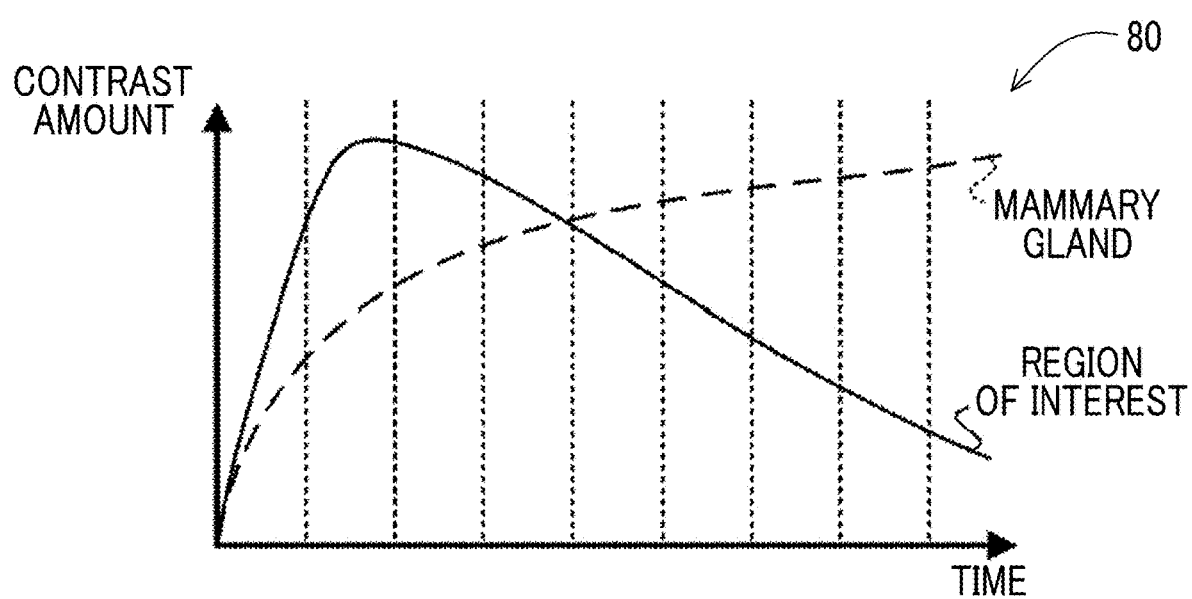
FIG. 11 is a diagram showing an example of information indicating a temporal change of a contrast amount.

FIG. 11 shows an example of information 80 indicating the temporal change of the contrast amount. In the information shown in FIG. 11, the horizontal axis represents the elapsed time since the contrast medium has been injected. In addition, the vertical axis represents the contrast amount. It should be noted that, as described above, the contrast amount in this case may not be the contrast amount itself, but may be the brightness value of the pixel. In the information shown in FIG. 11, a solid line shows an example of the temporal change of the contrast amount in a case in which the region of interest is a tumor, that is, a breast cancer. In addition, an example of the temporal change in the mammary gland region as the outside of the region of interest is shown by a dotted line. As shown in FIG. 11, in a case of the tumor, the contrast medium rapidly permeates and the contrast medium is washed out faster. Therefore, by observing the temporal change of the contrast amount of the region of interest, it can be used as an index for diagnosing whether or not the region of interest is the tumor and whether or not the region of interest is malignant. In addition, although there are individual differences in how the contrast medium is dyed, by comparing the temporal change of the contrast amount of the region outside the region of interest, for example, the mammary gland region assumed to be normal with the temporal change of the contrast amount of the region of interest, the speed at which the contrast medium permeates and the speed at which the contrast medium is washed out can be made clearer.

In next step S208, the display control unit 69 performs control of displaying, on the display unit 58, the plurality of difference images 72 generated in step S204 and the information 80 indicating the temporal change of the contrast amount derived in step S206, and then the present difference image generation display processing ends. It should be noted that the display control unit 69 performs control of performing predetermined image processing of assisting the user in interpreting the image, such as gradation enhancement processing or frequency enhancement processing, on the plurality of difference images 72 generated in step S204 and displaying the plurality of difference images 72 which have been subjected to the image processing on the display unit 58.

Figure 12:
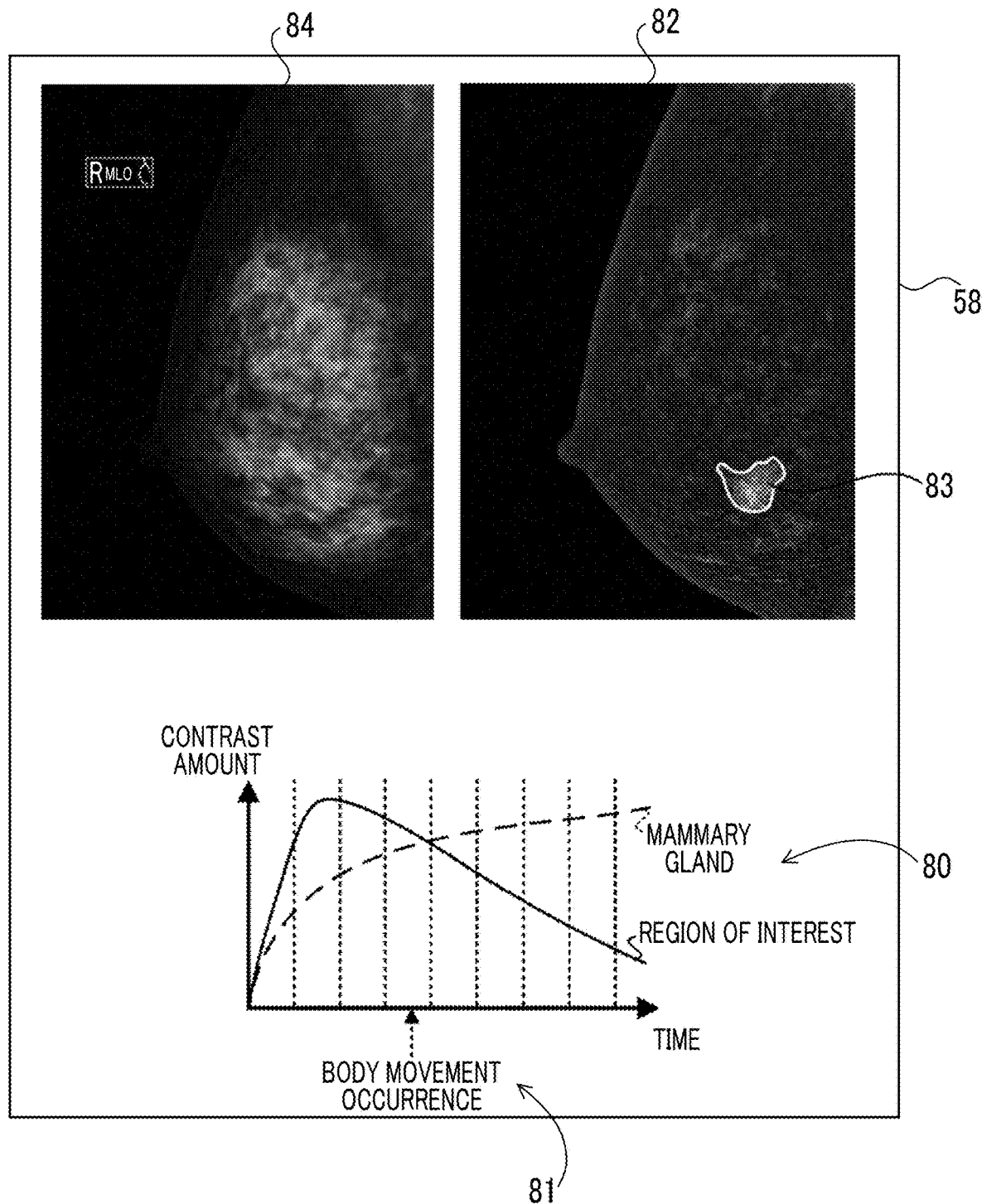
FIG. 12 is a diagram showing an example of a state in which the difference image and the information indicating the temporal change of the contrast amount are displayed on a display unit.

FIG. 12 shows an example of a state in which a moving image 82 and the information 80 indicating the temporal change of the contrast amount are displayed on the display unit 58. In the example shown in FIG. 12, information 81 indicating the timing at which the body movement of the breast has occurred is added to the information 80 indicating the temporal change of the contrast amount. In a case in which the low-energy image 70L is re-captured as described above, due to the influence of the body movement of the breast and the like, the positions of the skin line, the mammary gland structure, the region of interest, and the like may be deviated between the difference image 72 using the low-energy image 70L before the re-capturing and the difference image 72 using the low-energy image 70L after the re-capturing. Therefore, it is preferable that the user can recognize the timing at which the body movement of the breast has occurred, in other words, the timing at which the low-energy image 70L is captured. Therefore, as shown in FIG. 12, the display control unit 69 according to the present embodiment displays, on the display unit 58, the information 81 indicating the timing at which the body movement of the breast has occurred.

Figure 13:
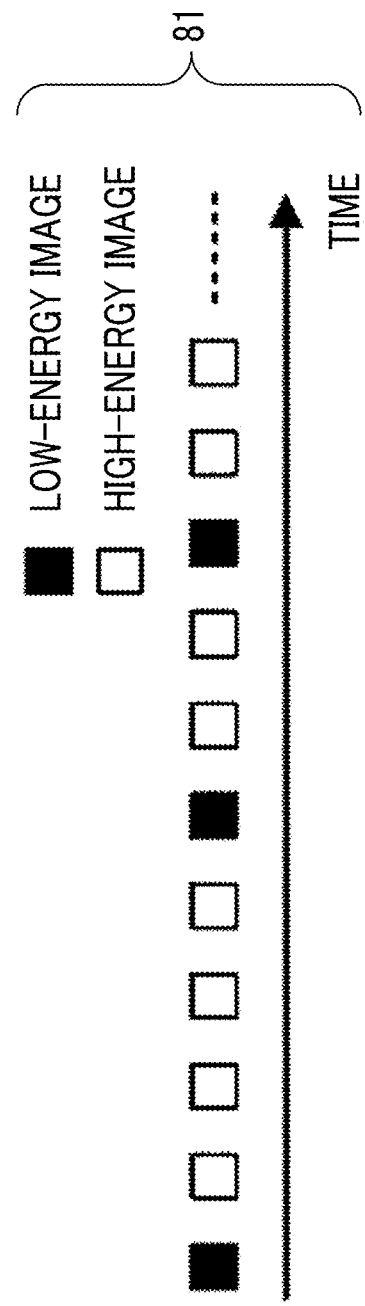
FIG. 13 is a diagram showing a display example of information indicating a timing at which a body movement of the breast has occurred.

It should be noted that the form in which the display control unit 69 displays, on the display unit 58, the information 81 indicating the timing at which the body movement of the breast has occurred is not limited to the form shown in FIG. 12. For example, as shown in FIG. 13, the information 81 indicating the timing at which the body movement of the breast has occurred may be displayed as a form in which an order in which the low-energy images 70L and the high-energy images 70H are captured is represented along with the elapsed time. As shown in FIG. 13, in a case in which the information 81 indicating the timing at which the body movement of the breast has occurred is displayed, the user can recognize a timing at which the low-energy image 70L is re-captured as the timing at which the body movement of the breast has occurred.

In addition, a form may be adopted in which the information 81 indicating the timing at which the body movement of the breast has occurred is displayed by a marker or the like in the moving image 82 described below. Specifically, the marker or the like may be displayed as the information 81 indicating the timing at which the body movement of the breast has occurred, on the difference image 72 using the high-energy image 70H in which the body movement amount of the breast exceeds the threshold value among the plurality of difference images 72 constituting the moving image 82.

In addition, as described above, the display control unit 69 according to the present embodiment continuously displays, on the display unit 58, the plurality of difference images 72 as the moving image 82 in the time series order of capturing. In the example shown in FIG. 12, positional information 83 indicating a position of the region of interest is also displayed on the difference image 72 as the moving image 82.

It should be noted that, in a case in which the moving image 82 is displayed, a timing for displaying the next difference image 72 may be changed according to a contrast value of the region of interest. For example, in a case in which the contrast value of the region of interest is equal to or greater than a threshold value, the timing for displaying the next difference image 72 may be delayed, that is, the display speed of the moving image may be made slower than in a case in which the contrast value is smaller than the threshold value. In addition, the display speed of the moving image 82 may be adjustable by the user.

It should be noted that the difference image 72 displayed by the display control unit 69 is not limited to a form of the moving image 82. For example, a form may be adopted in which, among the plurality of difference images 72 generated by the generation unit 68, a difference image 72 having a highest contrast of the region of interest is displayed. In addition, for example, a form may be adopted in which, by displaying a radiation image 84 described below or the low-energy image 70L, the difference image 72 having the highest contrast of a region designated by the user on the radiation image 84 or the low-energy image 70L is displayed.

In addition, as shown in FIG. 12, the display control unit 69 according to the present embodiment also displays the radiation image 84 on the display unit 58 as a comparative example in a case in which there is the radiation image 84 captured by the general imaging for the breast which is the subject, in other words, the radiation image 84 captured in a state in which the contrast medium has not been injected. It should be noted that, in the example shown in FIG. 12, the form has been described in which the moving image 82 and the radiation image 84 are displayed side by side, a form may be adopted in which any one of the moving image 82 or the radiation image 84 is displayed and the image to be displayed is switched according to the instruction of the user.

It should be noted that the radiation image displayed by the display control unit 69 on the display unit 58 is not limited to the image described above. For example, a form may be adopted in which, in addition to the difference image 72, at least one of the low-energy image 70L or the high-energy image 70H is displayed.

In addition, the image and the information displayed by the display control unit 69 on the display unit 58 are not limited to the image and the information described above. For example, a numerical value indicating the contrast amount of the region of interest may be displayed. In this case, the contrast amount may be the contrast amount of the entire region of interest, or may be any of an average value, a median value, or a maximum value of the contrast amount of the region of interest.

In this way, in a case in which the difference image generation display processing shown in FIG. 10 ends, the difference image generation display processing in step S16 shown in FIG. 8 ends. As a result, the series of processing related to the contrast imaging in the radiography system 1 according to the present embodiment ends. It should be noted that a form may be adopted in which the low-energy image 70L and the plurality of high-energy images 70H, which are captured by the mammography apparatus 10 according to the present embodiment, the plurality of difference images 72, the moving image 82, and the information 80 indicating the temporal change of the contrast amount, which are generated by the console 12, and the like are stored in the storage unit 52 of the console 12, picture archiving and communication systems (PACS), or the like.

In addition, in each form described above, the form has been described in which the difference image generation display processing is continuously performed after the contrast imaging control processing which is the processing of S14 in FIG. 8 ends, in other words, after the contrast imaging ends, but the timing for performing the difference image generation display processing, that is, the timing for generating the difference image 72 or displaying the difference image 72 is not limited to the present form. For example, a form may be adopted in which the timing of each of the generation of the difference image 72 and the display of the difference image 72 is a timing according to the user's desire after the contrast imaging.

As described above, the console 12 of each form described above comprises the CPU 50A as at least one processor. The CPU 50A acquires the low-energy image 70L captured by the mammography apparatus 10 by emitting the radiation R having the first energy to the breast into which the contrast medium has been injected. In addition, the CPU 50A sequentially acquires each of the plurality of high-energy images 70H captured by the mammography apparatus 10 at different timings by emitting the radiation R having the second energy higher than the first energy to the breast into which the contrast medium has been injected. In addition, the CPU 50A sequentially derives the body movement amount of the breast from each of the plurality of high-energy images 70H, and performs, in a case in which the derived body movement amount exceeds the threshold value, control of causing the mammography apparatus 10 to re-capture the low-energy image 70L before the next high-energy image 70H is captured. In addition, the CPU 50A generates the plurality of difference images 72 showing the difference between the low-energy image 70L and each of the plurality of high-energy images 70H.

As described above, with the console 12 according to the present embodiment, in a case in which the body movement amount exceeds the threshold value, the mammography apparatus 10 re-captures the low-energy image 70L, so that the influence of the body movement of the subject in the contrast imaging can be reduced. In addition, the radiation R having high energy is easily transmitted through fat, and an exposure dose of the subject is reduced as compared with the radiation R having low energy. Therefore, according to the present embodiment, the number of times of capturing of the low-energy image 70L can be made smaller than the number of times of capturing of the high-energy image 70H, so that the exposure dose of the subject can be reduced.

It should be noted that, in the form described above, as shown in FIGS. 7A and 7B, the form has been described in which the generation unit 68 generates the difference image 72 between the low-energy image 70L and the high-energy images 70H captured before the next low-energy image 70L is captured, but a combination of the low-energy image 70L and the high-energy image 70H for generating the difference image 72 is not limited to the present form.

Figure 14:
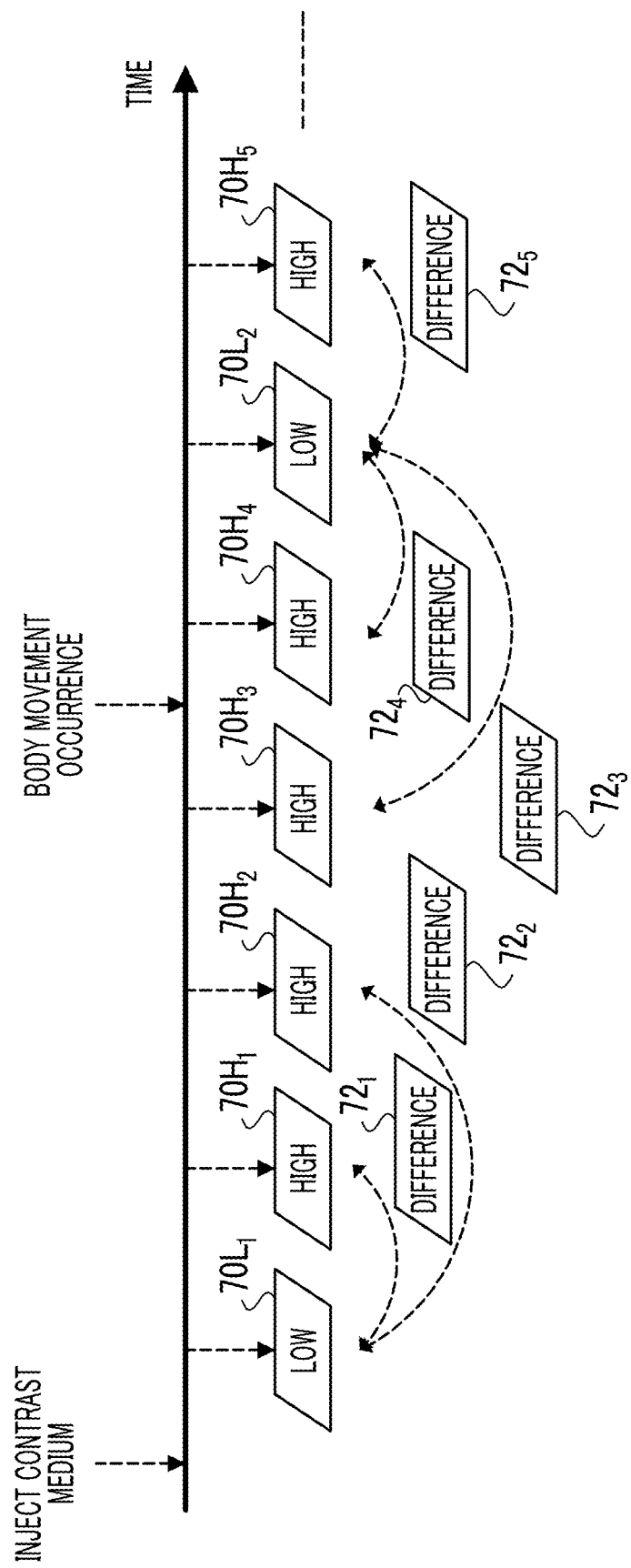
FIG. 14 is a diagram for describing another example of the generation method of the difference image.

For example, a form may be adopted in which the difference image with the low-energy image having the imaging timing closest to the high-energy image is generated. Specifically, as shown in FIG. 14, the generation unit 68 generates the difference image 721 between the high-energy image $70H_1$ and the low-energy image $70L_1$, and generates the difference image 722 between the high-energy image $70H_2$ and the low-energy image $70L_1$. In addition, the generation unit 68 generates the difference image 723 between the high-energy image $70H_3$ and the low-energy image $70L_2$, generates the difference image 724 of the high-energy image $70H_4$ and the low-energy image $70L_2$, and generates the difference image 725 between the high-energy image $70H_5$ and the low-energy image $70L_2$. In this way, the influence of the body movement can be reduced by generating the difference image by combining the low-energy image captured at the timing closest to the imaging timing of the high-energy image.

Figure 15:
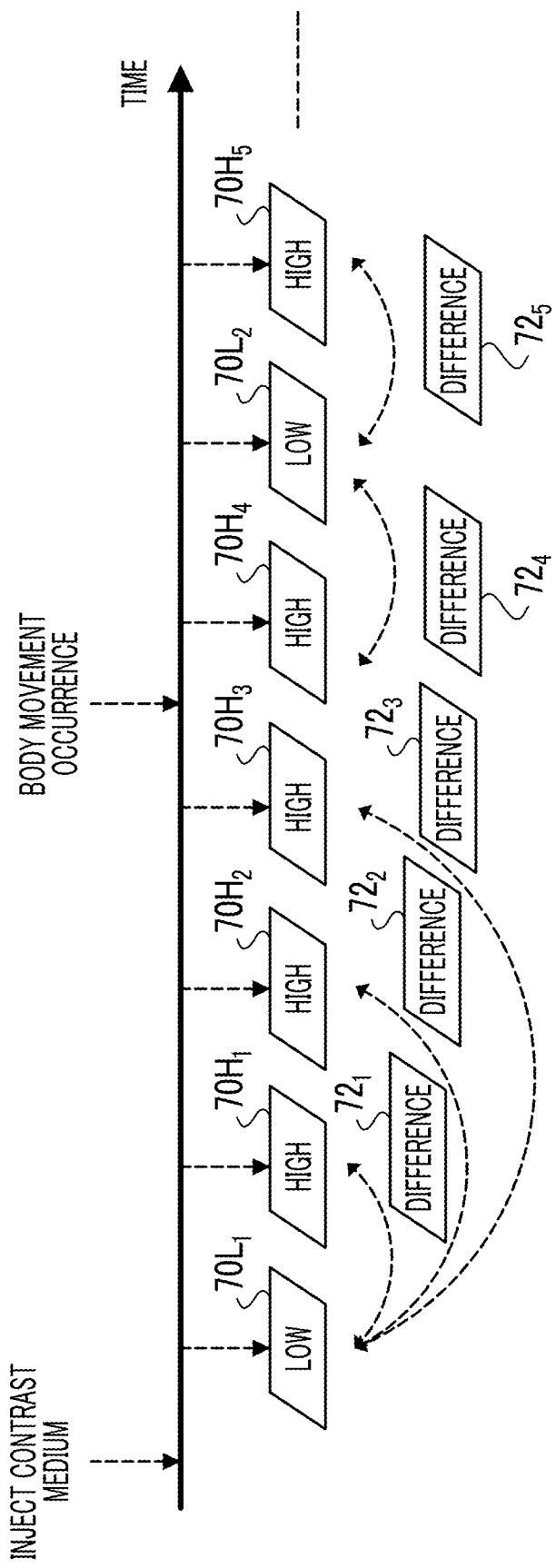
FIG. 15 is a diagram for describing still another example of the generation method of the difference image.

In addition, for example, the low-energy image 70L used for generating the difference image 72 may be switched with the timing at which the body movement of the breast has occurred as a reference. An example of this case is shown in FIG. 15. In the example shown in FIG. 15, the generation unit 68 generates the difference image 724 between the high-energy image $70H_4$ and the low-energy image $70L_2$. On the other hand, in the example shown in FIG. 7A described above, the generation unit 68 generates the difference image 724 between the high-energy image $70H_4$ and the low-energy image $70L_1$. As described above, for the high-energy image 70H captured after the body movement of the breast has occurred, the influence of the body movement can be further reduced by generating the difference image 72 showing the difference from the re-captured low-energy image 70L.

In addition, in the form described above, the form has been described in which, as described with reference to FIG. 6, the derivation unit 62 derives the body movement amount based on the difference images for body movement analysis 711 to 714 showing the difference between the high-energy images $70H_1$ to $70H_5$ which are continuous in time series, but a method by which the derivation unit 62 derives the body movement amount of the breast is not limited to the present form.

For example, a form may be adopted in which the derivation unit 62 uses the low-energy image 70L as a reference and derives the body movement amount of the breast based on the deviation of the high-energy image 70H from the reference. Specifically, a form can be adopted in which the derivation unit 62 uses a position of a specific structure, such as the region of interest or the mammary gland, in the low-energy image 70L as a reference, derives a movement vector of the specific structure in the high-energy image 70H, and detects that the body movement of the breast has occurred in a case in which magnitude of the derived movement vector exceeds a threshold value.

In addition, in the form described above, the form has been described in which the breast is applied as an example of the subject according to the present disclosure, and the mammography apparatus 10 is applied as an example of the radiography apparatus according to the present disclosure, but the subject is not limited to the breast, and the radiography apparatus is not limited to the mammography apparatus. For example, the subject may be a chest, an abdomen, or the like, and a form may be adopted in which a radiography apparatus other than the mammography apparatus is applied as the radiography apparatus.

In addition, in the form described above, the form has been described in which the console 12 is an example of the control apparatus according to the present disclosure, but an apparatus other than the console 12 may have the function of the control apparatus according to the present disclosure. In other words, some or all of the functions of the acquisition unit 60, the derivation unit 62, the control unit 64, the notification unit 66, the generation unit 68, and the display control unit 69 may be provided in an apparatus other than the console 12, for example, the mammography apparatus 10 or an external apparatus.

In addition, in the form described above, various processors shown below can be used as the hardware structure of processing units that execute various pieces of processing, such as the acquisition unit 60, the derivation unit 62, the control unit 64, the notification unit 66, the generation unit 68, and the display control unit 69. As described above, the various processors include, in addition to the CPU which is a general-purpose processor which executes software (program) and functions as various processing units, a programmable logic device (PLD) which is a processor of which a circuit configuration can be changed after manufacture, such as a field programmable gate array (FPGA), and a dedicated electric circuit which is a processor having a circuit configuration which is designed for exclusive use in order to execute specific processing, such as an application specific integrated circuit (ASIC).

One processing unit may be composed of one of the various processors or may be composed of a combination of two or more processors of the same type or different types (for example, a combination of a plurality of FPGAs or a combination of a CPU and an FPGA). In addition, a plurality of processing units may be composed of one processor.

A first example of the configuration in which the plurality of processing units are composed of one processor is a form in which one processor is composed of a combination of one or more CPUs and software and the processor functions as the plurality of processing units, as represented by the computer, such as a client and a server. Second, as represented by a system on chip (SoC) or the like, there is a form of using a processor that realizes the function of the entire system including the plurality of processing units by one integrated circuit (IC) chip. As described above, various processing units are composed of one or more of the various processors as the hardware structure.

Further, more specifically, an electric circuit (circuitry) obtained by combining circuit elements, such as semiconductor elements, can be used as the hardware structure of the various processors.

In addition, in each embodiment described above, the aspect has been described in which the contrast imaging control processing program 51A and the difference image generation display processing program 51B are stored (installed) in advance, but the present disclosure is not limited to this. Each of the contrast imaging control processing program 51A and the difference image generation display processing program 51B may be provided in a form being recorded in the recording medium, such as a compact disc read only memory (CD-ROM), a digital versatile disc read only memory (DVD-ROM), and a universal serial bus (USB) memory. In addition, a form may be adopted in which each of the contrast imaging control processing program 51A and the difference image generation display processing program 51B is downloaded from an external apparatus via a network.

The disclosure of JP2020-162695 filed on Sep. 28, 2020 is incorporated in the present specification by reference in its entirety.

All documents, patent applications, and technical standards described in the present specification are incorporated in the present specification by reference to the same extent as a case in which each document, patent application, and technical standard are specifically and individually noted to be incorporated by reference.

What is claimed is:

1. A control apparatus comprising:
at least one processor that is configured to:
capture a low-energy image by a radiography apparatus by emitting radiation having first energy to a subject into which a contrast medium has been injected, and then sequentially acquires each of a plurality of high-energy images captured by the radiography apparatus at different timings by emitting radiation having second energy higher than the first energy to the subject into which the contrast medium has been injected,
sequentially derive a body movement amount of the subject from each of the plurality of high-energy images, and
perform, in a case in which the derived body movement amount exceeds a threshold value, control of causing the radiography apparatus to re-capture the low-energy image before a next high-energy image is captured.

2. The control apparatus according to claim 1,
wherein the at least one processor is configured to generate a plurality of difference images showing a difference between the low-energy image and each of the plurality of high-energy images.

3. The control apparatus according to claim 2,
wherein the at least one processor is configured to generate a difference image showing a difference from the low-energy image captured at a timing closest to an imaging timing of the high-energy image.

4. The control apparatus according to claim 2,
wherein the at least one processor is configured to generate a difference image showing a difference from the re-captured low-energy image from a high-energy image in which the derived body movement amount exceeds the threshold value.

5. The control apparatus according to claim 2,
wherein the at least one processor is configured to switch the low-energy image to be used for generating the difference image with a timing at which a body movement of the subject has occurred as reference.

6. The control apparatus according to claim 2,
wherein the at least one processor is configured to:
generate a first difference image showing a difference from a high-energy image having an imaging timing closest to an imaging timing of the low-energy image,
generate a second difference image showing a difference between the high-energy images, and
generates the plurality of difference images by using the first difference image and the second difference image.

7. The control apparatus according to claim 2,
wherein the at least one processor is configured to:
generate a difference image for body movement analysis showing a difference between two continuously captured high-energy images among the plurality of high-energy images, and
sequentially derive the body movement amount of the subject from the generated difference image for body movement analysis.

8. The control apparatus according to claim 1,
wherein the at least one processor is configured to sequentially derive the body movement amount of the subject from each of the plurality of high-energy images with the low-energy image as a reference.

9. The control apparatus according to claim 2,
wherein the at least one processor is configured to generate the plurality of difference images after performing registration between the low-energy image and each of the plurality of high-energy images.

10. The control apparatus according to claim 9,
wherein the at least one processor is configured to perform registration between a region of interest in the low-energy image and a region of interest in each of the plurality of high-energy images.

11. The control apparatus according to claim 1,
wherein the at least one processor is configured to:
correct each of the plurality of high-energy images according to the body movement amount, and
generate a plurality of difference images showing a difference between the low-energy image and each of the corrected plurality of high-energy images.

12. The control apparatus according to claim 1,
wherein the at least one processor is configured to give a notification that a body movement has occurred in a case in which the derived body movement amount exceeds the threshold value.

13. The control apparatus according to claim 2,
wherein the at least one processor is configured to continuously display the plurality of difference images as a moving image in a time series order of capturing.

14. The control apparatus according to claim 2,
wherein the at least one processor is configured to display a difference image having a highest contrast of a region of interest among the plurality of difference images.

15. The control apparatus according to claim 2,
wherein the at least one processor is configured to:
derive a contrast amount of a region of interest in each of the plurality of difference images, and
generate information indicating a temporal change of the contrast amount of the region of interest and displays the generated information.

16. The control apparatus according to claim 1,
wherein the subject is a breast, and
the radiography apparatus is a mammography apparatus.

17. A control method executed by a computer, the method comprising:
acquiring a low-energy image captured by a radiography apparatus by emitting radiation having first energy to a subject into which a contrast medium has been injected;
sequentially acquiring each of a plurality of high-energy images captured by the radiography apparatus at different timings by emitting radiation having second energy higher than the first energy to the subject into which the contrast medium has been injected;
sequentially deriving a body movement amount of the subject from each of the plurality of high-energy images; and
performing, in a case in which the derived body movement amount exceeds a threshold value, control of causing the radiography apparatus to re-capture the low-energy image before a next high-energy image is captured.

18. A non-transitory storage medium storing a control program causing a computer to execute a control processing, the control processing comprising:
acquiring a low-energy image captured by a radiography apparatus by emitting radiation having first energy to a subject into which a contrast medium has been injected;
sequentially acquiring each of a plurality of high-energy images captured by the radiography apparatus at different timings by emitting radiation having second energy higher than the first energy to the subject into which the contrast medium has been injected;

sequentially deriving a body movement amount of the subject from each of the plurality of high-energy images; and performing, in a case in which the derived body movement amount exceeds a threshold value, control of causing the radiography apparatus to re-capture the low-energy image before a next high-energy image is captured.

* * * * *